United States Patent
Chandrasekaran et al.

(10) Patent No.: US 10,704,172 B2
(45) Date of Patent: Jul. 7, 2020

(54) FIBERS AND ARTICLES INCLUDING THEM

(71) Applicant: 3M INNOVATIVE PROPERTIES COMPANY, St. Paul, MN (US)

(72) Inventors: Neelakandan Chandrasekaran, Woodbury, MN (US); Lori-Ann S. Prioleau, St. Paul, MN (US); Leigh E. Wood, Woodbury, MN (US); Jayant Chakravarty, Woodbury, MN (US); Timothy V. Stagg, Hudson, WI (US)

(73) Assignee: 3M Innovative Properties Company, St. Paul, MN (US)

( * ) Notice: Subject to any disclaimer, the term of this patent is extended or adjusted under 35 U.S.C. 154(b) by 824 days.

(21) Appl. No.: 15/302,860

(22) PCT Filed: Apr. 10, 2015

(86) PCT No.: PCT/US2015/025250
§ 371 (c)(1),
(2) Date: Oct. 7, 2016

(87) PCT Pub. No.: WO2015/157602
PCT Pub. Date: Oct. 15, 2015

(65) Prior Publication Data
US 2017/0029991 A1    Feb. 2, 2017

Related U.S. Application Data

(60) Provisional application No. 61/978,119, filed on Apr. 10, 2014.

(51) Int. Cl.
*D04H 1/541*    (2012.01)
*A61F 13/15*    (2006.01)
(Continued)

(52) U.S. Cl.
CPC ........... *D04H 1/541* (2013.01); *A61F 13/622* (2013.01); *A61F 13/84* (2013.01); *B32B 5/02* (2013.01);
(Continued)

(58) Field of Classification Search
CPC .................................................. D01D 5/247
See application file for complete search history.

(56) References Cited

U.S. PATENT DOCUMENTS 3,930,502 A    1/1976 Tritsch
4,118,531 A    10/1978 Hauser
(Continued)

FOREIGN PATENT DOCUMENTS

CN    101844070    9/2010
CN    102002848    4/2011
(Continued)

OTHER PUBLICATIONS

Chu, "Crystal transformation and micropore formation during uniaxial drawing of β-form polypropylene film", Polymer, 1995, vol. 36, No. 13, pp. 2523-2530.
(Continued)

*Primary Examiner* — Bradley H Philips

(57) ABSTRACT

A multi-component fiber including at least first and second components. In some cases, at least a portion of the first component is opaque and microporous, and the second component is different from the first component. In some cases, at least a portion of the second component can be seen through at least a portion of the first component. A fiber having an opaque, microporous region and a see-through region of lower porosity is also disclosed. Fibrous webs including such fibers are also disclosed. In some cases, the fibrous web has at least one first region where first portions of the multiple fibers are opaque and microporous and at (Continued)

least one second region where second portions of the multiple fibers form a see-through region of lower porosity. Articles and laminates including the fibrous webs are disclosed. Methods of making the fibers, fibrous webs, and articles are also disclosed.

14 Claims, 5 Drawing Sheets

(51) Int. Cl.
*B32B 5/14* (2006.01)
*D04H 1/4374* (2012.01)
*D04H 1/4382* (2012.01)
*D04H 1/46* (2012.01)
*A61F 13/62* (2006.01)
*D01D 5/247* (2006.01)
*D01F 1/10* (2006.01)
*D01F 8/00* (2006.01)
*D01F 8/06* (2006.01)
*B32B 7/02* (2019.01)
*B32B 27/12* (2006.01)
*B32B 27/32* (2006.01)
*B32B 5/26* (2006.01)
*B32B 27/30* (2006.01)
*B32B 27/34* (2006.01)
*B32B 27/08* (2006.01)
*B32B 7/12* (2006.01)
*B32B 27/36* (2006.01)
*B32B 5/02* (2006.01)
*B32B 5/08* (2006.01)
*B32B 5/24* (2006.01)
*B32B 27/28* (2006.01)
*B32B 27/20* (2006.01)
*B32B 19/04* (2006.01)
*B32B 27/06* (2006.01)
*B32B 27/18* (2006.01)
*B32B 19/06* (2006.01)
*A61F 13/84* (2006.01)

(52) U.S. Cl.
CPC .......... *B32B 5/022* (2013.01); *B32B 5/08* (2013.01); *B32B 5/142* (2013.01); *B32B 5/24* (2013.01); *B32B 5/26* (2013.01); *B32B 7/02* (2013.01); *B32B 7/12* (2013.01); *B32B 19/04* (2013.01); *B32B 19/06* (2013.01); *B32B 27/06* (2013.01); *B32B 27/08* (2013.01); *B32B 27/12* (2013.01); *B32B 27/18* (2013.01); *B32B 27/20* (2013.01); *B32B 27/28* (2013.01); *B32B 27/306* (2013.01); *B32B 27/308* (2013.01); *B32B 27/32* (2013.01); *B32B 27/34* (2013.01); *B32B 27/36* (2013.01); *B32B 27/365* (2013.01); *D01D 5/247* (2013.01); *D01F 1/10* (2013.01); *D01F 8/00* (2013.01); *D01F 8/06* (2013.01); *D04H 1/4374* (2013.01); *D04H 1/4382* (2013.01); *D04H 1/46* (2013.01); *A61F 2013/8497* (2013.01); *B32B 2262/00* (2013.01); *B32B 2262/02* (2013.01); *B32B 2262/023* (2013.01); *B32B 2262/0223* (2013.01); *B32B 2262/0238* (2013.01); *B32B 2262/0253* (2013.01); *B32B 2262/0261* (2013.01); *B32B 2262/0276* (2013.01); *B32B 2262/0292* (2013.01); *B32B 2262/12* (2013.01); *B32B 2264/00* (2013.01); *B32B 2264/02* (2013.01); *B32B 2307/40* (2013.01); *B32B 2307/402* (2013.01); *B32B 2307/41* (2013.01); *B32B 2307/412* (2013.01); *B32B 2307/51* (2013.01); *B32B 2307/726* (2013.01); *B32B 2307/7265* (2013.01); *B32B 2307/75* (2013.01); *B32B 2535/00* (2013.01); *B32B 2555/00* (2013.01); *B32B 2555/02* (2013.01)

(56) References Cited

U.S. PATENT DOCUMENTS

| | | |
|---|---|---|
| 4,215,682 A | 8/1980 | Kubik |
| 4,375,718 A | 3/1983 | Wadsworth |
| 4,406,850 A | 9/1983 | Hills |
| 4,435,141 A | 3/1984 | Weisner |
| 4,483,897 A | 11/1984 | Fujimura |
| 4,539,256 A | 9/1985 | Shipman |
| 4,592,815 A | 6/1986 | Nakao |
| 4,609,584 A | 9/1986 | Cutler et al. |
| 4,775,310 A | 10/1988 | Fischer |
| 4,839,131 A | 6/1989 | Cloeren |
| 4,874,659 A | 10/1989 | Ando |
| 4,902,553 A | 2/1990 | Hwang |
| 4,923,650 A | 5/1990 | Antoon, Jr. et al. |
| 5,120,594 A | 6/1992 | Mrozinski |
| 5,236,963 A | 8/1993 | Jacoby et al. |
| 5,256,231 A | 10/1993 | Gorman |
| 5,261,899 A | 11/1993 | Visscher |
| 5,276,083 A | 1/1994 | Kawauchi |
| 5,298,694 A | 3/1994 | Thompson |
| 5,387,207 A | 2/1995 | Dyer |
| 5,401,446 A | 3/1995 | Tsai |
| 5,411,693 A | 3/1995 | Wust, Jr. |
| 5,458,972 A | 10/1995 | Hagen |
| 5,491,188 A | 2/1996 | Ikeda |
| 5,503,907 A | 4/1996 | Gessner |
| 5,510,161 A | 4/1996 | Lloyd |
| 5,516,567 A | 5/1996 | Roessler |
| 5,569,234 A | 10/1996 | Buell |
| 5,572,291 A | 11/1996 | Moriguchi |
| 5,605,729 A | 2/1997 | Mody |
| 5,618,479 A | 4/1997 | Lijten |
| 5,897,541 A | 4/1999 | Uitenbroek |
| 5,989,004 A | 11/1999 | Cook |
| 6,074,018 A | 6/2000 | Zeiner |
| 6,074,590 A * | 6/2000 | Gownder .............. D01D 5/253 264/172.12 |
| 6,075,179 A | 6/2000 | McCormack |
| 6,110,588 A | 8/2000 | Perez |
| 6,190,758 B1 | 2/2001 | Stopper |
| 6,200,669 B1 | 3/2001 | Marmon |
| 6,240,817 B1 | 6/2001 | James et al. |
| 6,334,504 B1 | 1/2002 | Sato |
| 6,420,024 B1 | 7/2002 | Perez |
| 6,521,685 B1 | 2/2003 | Zhao |
| 6,544,633 B1 | 4/2003 | Ogura |
| 6,586,073 B2 | 7/2003 | Perez |
| 6,669,887 B2 | 12/2003 | Hilston |
| 6,719,742 B1 | 4/2004 | McCormack |
| 6,815,048 B2 | 11/2004 | Davidson |
| 6,828,019 B2 | 12/2004 | Kong |
| 6,861,132 B2 | 3/2005 | Ikeda |
| 7,168,139 B2 | 1/2007 | Seth |
| 7,185,761 B2 | 3/2007 | Molina |
| 7,220,478 B2 | 5/2007 | McCormack |
| 7,423,088 B2 | 9/2008 | Mäder |
| 7,682,689 B2 | 3/2010 | Sadamitsu et al. |
| 7,790,641 B2 | 9/2010 | Baker, Jr. et al. |
| 7,794,220 B2 | 9/2010 | Suzuki |
| 7,897,078 B2 | 3/2011 | Petersen |
| 7,981,336 B2 | 7/2011 | Pourdeyhimi |
| 8,021,996 B2 | 9/2011 | Walser |
| 8,191,709 B2 | 6/2012 | Molina |
| 8,324,444 B2 | 12/2012 | Hansson |
| 8,613,736 B2 | 12/2013 | Schnabel |
| 8,680,169 B2 | 3/2014 | Yamada |
| 9,278,471 B2 | 3/2016 | Chandrasekaran |
| 9,358,714 B2 | 6/2016 | Chandrasekaran |
| 10,376,420 B2 | 8/2019 | Chandrasekaran |

(56) References Cited

U.S. PATENT DOCUMENTS

| | | | |
|---|---|---|---|
| 2002/0062117 A1 | 5/2002 | Raufman | |
| 2003/0035943 A1 | 2/2003 | Jones | |
| 2003/0036577 A1* | 2/2003 | Hughes | B01D 67/0027 521/82 |
| 2003/0091617 A1 | 5/2003 | Mrozinski | |
| 2003/0091618 A1 | 5/2003 | Seth | |
| 2003/0148091 A1 | 8/2003 | Ikeda et al. | |
| 2003/0207137 A1 | 11/2003 | Kong et al. | |
| 2004/0209063 A1 | 10/2004 | Gallagher et al. | |
| 2005/0170726 A1* | 8/2005 | Brunson | A41D 13/11 442/327 |
| 2005/0215155 A1 | 9/2005 | Young et al. | |
| 2005/0215963 A1 | 9/2005 | Autran et al. | |
| 2005/0288510 A1 | 12/2005 | Mader et al. | |
| 2006/0024520 A1 | 2/2006 | Kong et al. | |
| 2006/0177632 A1 | 8/2006 | Jacoby | |
| 2007/0020448 A1 | 1/2007 | Hubbard | |
| 2007/0082154 A1 | 4/2007 | Ambroise | |
| 2007/0100306 A1 | 5/2007 | DiZio | |
| 2007/0286976 A1 | 12/2007 | Selen | |
| 2008/0000581 A1 | 1/2008 | Nison | |
| 2008/0000793 A1 | 1/2008 | Lambertus | |
| 2008/0044617 A1 | 2/2008 | Schmitz | |
| 2008/0233373 A1 | 9/2008 | Coburn | |
| 2009/0258212 A1 | 10/2009 | Jacoby | |
| 2009/0258560 A1 | 10/2009 | Kristiansen | |
| 2010/0010168 A1 | 1/2010 | Wolfschwenger et al. | |
| 2010/0301510 A1 | 12/2010 | Coburn | |
| 2011/0088828 A1 | 4/2011 | Misek | |
| 2011/0147475 A1 | 6/2011 | Biegler | |
| 2011/0151171 A1 | 6/2011 | Biegler | |
| 2011/0264064 A1 | 10/2011 | Arora | |
| 2012/0220973 A1 | 8/2012 | Chan | |
| 2012/0231692 A1 | 9/2012 | Peyras-Carratte et al. | |
| 2012/0242009 A1 | 9/2012 | Mullane | |
| 2012/0308755 A1 | 12/2012 | Gorman | |
| 2012/0329647 A1 | 12/2012 | Nellenbach | |
| 2013/0202828 A1 | 8/2013 | Jacoby | |
| 2013/0281950 A1 | 10/2013 | Digiacomantonio | |
| 2014/0044934 A1 | 2/2014 | Bills | |
| 2014/0093716 A1 | 4/2014 | Hanschen | |
| 2014/0343526 A1* | 11/2014 | Knapmeyer | D04H 1/541 604/385.25 |
| 2015/0157514 A1* | 6/2015 | Cinquemani | D04H 3/007 604/369 |
| 2016/0101208 A1* | 4/2016 | Topolkaraev | B29C 48/91 604/370 |

FOREIGN PATENT DOCUMENTS

| | | |
|---|---|---|
| DE | 3831580 | 4/1989 |
| DE | 102007050047 | 4/2009 |
| EP | 0341993 | 11/1989 |
| EP | 0539504 | 5/1993 |
| EP | 0581323 | 2/1994 |
| EP | 0925769 | 6/1999 |
| EP | 0974326 | 1/2000 |
| EP | 1816158 | 8/2007 |
| FR | 2018634 | 6/1970 |
| FR | 2083552 | 12/1971 |
| GB | 2252838 | 8/1992 |
| GB | 2252839 | 8/1992 |
| GB | 2323325 | 9/1998 |
| GB | 2323327 | 9/1998 |
| JP | 59-137552 | 8/1984 |
| JP | 61-275434 | 12/1986 |
| JP | 62-57920 | 3/1987 |
| JP | 62-141120 | 6/1987 |
| JP | 62-199833 | 9/1987 |
| JP | 06033022 | 8/1994 |
| JP | 10085257 A * | 4/1998 |
| JP | 10114357 | 5/1998 |
| JP | 2000169608 | 6/2000 |
| JP | 2002-315607 | 10/2002 |
| JP | 2003-166125 | 6/2003 |
| JP | 3414494 | 6/2003 |
| JP | 2005-279005 | 10/2005 |
| JP | 2005-305817 | 11/2005 |
| JP | 2006-314361 | 11/2006 |
| JP | 2009-503279 | 1/2009 |
| WO | 1992-15734 | 9/1992 |
| WO | 1994-06387 | 3/1994 |
| WO | 9605262 | 2/1996 |
| WO | 2003-086257 | 10/2003 |
| WO | 2004-075803 | 9/2004 |
| WO | 2006-023442 | 3/2006 |
| WO | 2006-073919 | 7/2006 |
| WO | 2007-016480 | 2/2007 |
| WO | 2007-032965 | 3/2007 |
| WO | 2009-040767 | 4/2009 |
| WO | 2010-065602 | 6/2010 |
| WO | 2011-119323 | 9/2011 |
| WO | 2013-152287 | 10/2013 |
| WO | 2014-201219 | 12/2014 |
| WO | 2014-201229 | 12/2014 |

OTHER PUBLICATIONS

Chu, "Microvoid formation process during the plastic deformation of β-form polypropylene", Polymer, 1994, vol. 35, No. 16, pp. 3442-3448.

Jones, "Crystalline forms of isotactic polypropylene", 1964, vol. 75, No. 1, pp. 134-158.

International Search Report for PCT International Application No. PCT/US2015/025250 dated Jul. 16, 2015, 3 pages.

Wang Xiaoyan, Development of β-crystalline polypropylene microporous fiber, China Synthetic Fiber Industry, vol. 34(1), 2011, pp. 16-19.

* cited by examiner

FIBERS AND ARTICLES INCLUDING THEM

CROSS-REFERENCE TO RELATED APPLICATION

This application is a national stage filing under 35 U.S.C. 371 of PCT/US2015/025250, filed Apr. 10, 2015, which claims priority to U.S. Application No. 61/978,119, filed Apr. 10, 2014, the disclosure of which is incorporated by reference in its entirety herein.

BACKGROUND

Polymer fibers are useful in a variety of products including medical and hygiene products, carpets and floor coverings, apparel and household textiles, filtering media, agro- and geotextiles, automotive interior, filler for sleeping bags, comforters, pillows, and cushions, cleaning wipes, abrasive articles, and numerous others.

A polypropylene fiber including a beta-nucleating agent having a porous structure for use in filters is disclosed in DE 102007050047, published Apr. 23, 2009.

Various multi-component fibers are known. Examples include fibers that have a low temperature melting or softening sheath covering a higher melting core. Multi-component structures may be useful, for example, for fiber bonding, wherein the sheath, for example, when melted or softened serves as a bonding agent to bond individual fibers together.

In other technologies, a variety of different personal hygiene articles (e.g., absorbent articles such as diapers, adult incontinence products, and sanitary napkins) that include different printed and/or colored regions are available in the market. Printing or coloring on such articles can be attractive to the consumer and help the consumer differentiate between different brands. Some manufacturers of absorbent articles print with multi-colored graphics that are a signature of their brand. Others may use monochromatic printing on the articles. Printing approaches to providing a differentiated product generally use ink, colored adhesives, or heat- or pressure-activated chemical colorants, each of which adds cost to the product that is passed on to consumers. Some recent examples of absorbent articles with patterns or colors include those described in U.S. Pat. No. 8,324,444 (Hansson et al.) and U.S. Pat. Appl. Pub. Nos. 2011/0264064 (Arora et al.) and 2012/0242009 (Mullane et al.).

SUMMARY

The present disclosure provides fibers that are typically at least partially microporous and fibrous webs including them. The fibrous web typically has a first region in which portions of the fibers are opaque and microporous and a second region in which portions of the fibers form at least one see-through region of lower porosity. The see-through region of lower porosity typically has a predetermined (in other words, designed) shape. Advantageously, the see-through region can be in the form of a wide variety of patterns, numbers, pictures, symbols, alphabetical letters, bar code, or combinations thereof that can be selected to be aesthetically pleasing to a user. The see-through region can also be in the form of a company name, brand name, or logo that may be readily identified by a customer. Personal hygiene articles including these fibrous webs are also described. The personal hygiene article can be readily customized depending on the requirements of a particular product. The see-through region provides a visual image without the use of inks or other expensive, color-providing chemicals.

In one aspect, the present disclosure provides a multi-component fiber having at least first and second components. At least a portion of the first component is opaque and microporous, and the second component is different from the first component.

In another aspect, the present disclosure provides a multi-component fiber having at least first and second components. At least a portion of the second component can be seen through at least a portion of the first component. In some embodiments, the first component includes polypropylene and a beta-nucleating agent.

In another aspect, the present disclosure provides a fiber having an opaque, microporous region and a see-through region of lower porosity.

In another aspect, the present disclosure provides a fibrous web including multiple fibers of any one of the aforementioned aspects.

In another aspect, the present disclosure provides a fibrous web of multiple fibers. The fibrous web has at least one first region in which first portions of the multiple fibers are opaque and microporous and at least one second region in which second portions of the multiple fibers form a see-through region of lower porosity than the first portions. The fibrous web may be, for example, a first layer of a laminate having the first layer and a second layer, where a portion of the second layer is visible through the second portions of the multiple fibers.

In another aspect, the present disclosure provides a personal hygiene article having a chassis with a topsheet, a backsheet, an absorbent component between the topsheet and the backsheet, and the fibrous web of any of the aforementioned aspects.

In another aspect, the present disclosure provides a personal hygiene article comprising a chassis with a topsheet, a backsheet, an absorbent component between the topsheet and the backsheet. The personal hygiene article includes a fiber wherein at least a portion of the fiber is opaque and microporous.

In another aspect, the present disclosure provides a method of making a multi-component fiber described above. The method includes spinning a multi-component fiber having a first component and a second component. The first component includes at least one of a beta-nucleating agent, a diluent, or a cavitating agent. The second component is different from the first component. The method further includes stretching the fiber to provide microporosity in at least the first component.

In another aspect, the present disclosure provides a method of making the fiber described above. The method includes providing a fiber, at least a portion of which is microporous, and collapsing at least some pores in the fiber to form at least one see-through region.

In another aspect, the present disclosure provides a method of making the fibrous web described above. The method includes providing the fibrous web, at least a portion of which is microporous, and collapsing at least some pores in the fibrous web to form at least one see-through region. The fibrous web has at least one first region in which first portions of the multiple fibers are opaque and microporous and at least one second region in which second portions of the multiple fibers form a see-through region of lower porosity than the first portions.

In another aspect, the present disclosure provides a method of making a personal hygiene article. The method includes incorporating the fibrous web described above into the personal hygiene article.

In this application, terms such as "a", "an" and "the" are not intended to refer to only a singular entity, but include the general class of which a specific example may be used for illustration. The terms "a", "an", and "the" are used interchangeably with the term "at least one". The phrases "at least one of" and "comprises at least one of" followed by a list refers to any one of the items in the list and any combination of two or more items in the list. All numerical ranges are inclusive of their endpoints and non-integral values between the endpoints unless otherwise stated.

The terms "first" and "second" are used in this disclosure in their relative sense only. It will be understood that, unless otherwise noted, those terms are used merely as a matter of convenience in the description of one or more of the embodiments.

The term "microporous" refers to having multiple pores that have an average dimension (in some cases, diameter) of up to 10 micrometers. At least some of the multiple pores should have a dimension on the order of or larger than the wavelength of visible light. For example, at least some of the pores should have a dimension (in some cases, diameter) of at least 400 nanometers. Pore size is measured by measuring bubble point according to ASTM F-316-80. The pores may be open cell pores or closed cell pores. In some embodiments, the pores are closed cell pores.

A fiber having a microporous region will be understood to have pores in the polymer of the fiber in that region. Such microporosity does not refer to the interstices of the multiple fibers of a fibrous web.

The term "see-through" refers to either transparent (that is, allowing passage of light and permitting a clear view of objects beyond) or translucent (that is, allowing passage of light and not permitting a clear view of objects beyond). The see-through region may be colored or colorless. It should be understood that a "see-through" region is large enough to be seen by the naked eye.

"Multi-component" refers to fiber having a cross-section comprising two or more discrete polymer components, two or more discrete blends of polymer components, or at least one discrete polymer component and at least one discrete blend of polymer components. "Multi-component fiber" includes, but is not limited to, "bicomponent fiber." A multi-component fiber may have an overall cross section divided into subsections of the differing components of any shape or arrangement, including, for example, coaxial subsections, concentric core-and-sheath subsections, eccentric core-and-sheath subsections, side-by-side subsections, islands-in the sea subsection, segmented pie subsections, etc.

A "sheath" is understood to substantially surround a core or cores. In some embodiments, the sheath may extend around at least 75, 80, 85, 90, 95, 97, or 99 percent of the outer surface of core or cores. The sheath may also completely surround the core or cores.

The term "nonwoven" when referring to a fibrous web means having a structure of individual fibers or threads which are interlaid, but not in an identifiable manner as in a knitted fabric. Nonwoven fabrics or webs can be formed from various processes such as meltblowing processes, spunbonding processes, spunlacing processes, and bonded carded web processes.

The above summary of the present disclosure is not intended to describe each disclosed embodiment or every implementation of the present disclosure. The description that follows more particularly exemplifies illustrative embodiments. It is to be understood, therefore, that the drawings and following description are for illustration purposes only and should not be read in a manner that would unduly limit the scope of this disclosure.

BRIEF DESCRIPTION OF THE DRAWINGS

The disclosure may be more completely understood in consideration of the following detailed description of various embodiments of the disclosure in connection with the accompanying drawings, in which.

DETAILED DESCRIPTION

Figure 1A:
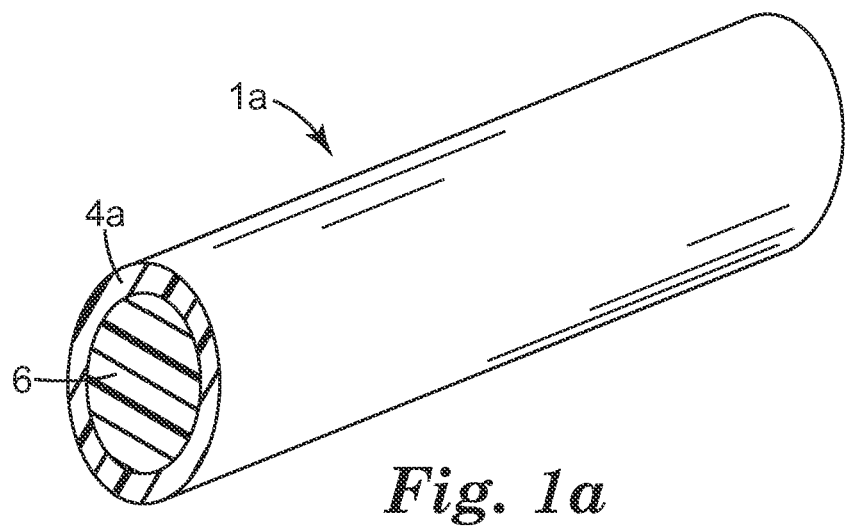
FIG. 1a is a perspective view of an embodiment of a multi-component fiber according to the present disclosure.

An embodiment of a fiber according to the present disclosure is shown in FIG. 1a. Fiber 1a is a multi-component fiber having a generally cylindrical shape, sheath 4a as a first component, and core 6 as a second component. In fibers according to the present disclosure, the first and second components typically comprise a first polymeric composition and a second polymeric composition, respectively, wherein the first and second polymeric compositions are different. In fiber 1a, sheath 4a is opaque and microporous, and core 6 has a different composition that is not microporous and is a different color from sheath 4a. Although in the perspective view of FIG. 1a, both the sheath 4a and core 6 are shown at the end of the fiber, from other viewing angles, the core 6 and its color are hidden by the opaque sheath 4a.

Figure 1B:
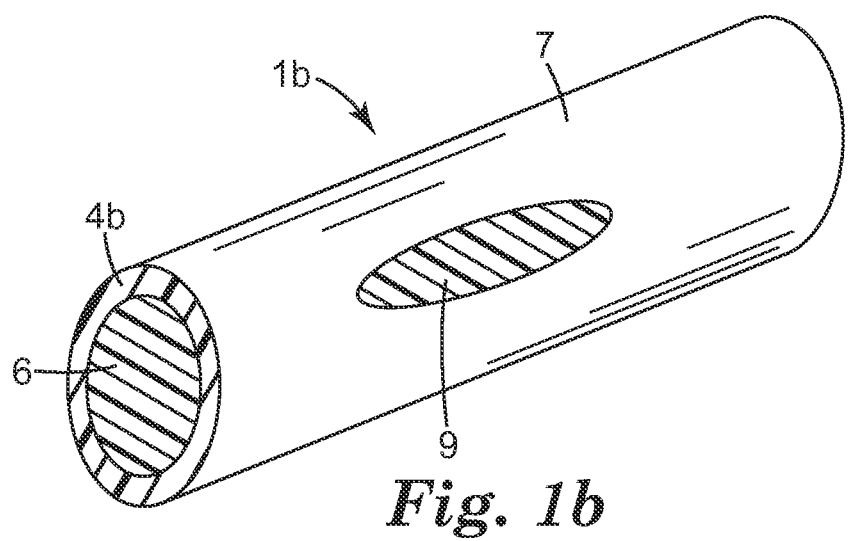
FIG. 1b is a perspective view of another embodiment of a fiber according to the present disclosure, which is a multi-component fiber.

Another embodiment of a fiber according to the present disclosure is shown in FIG. 1b. FIG. 1b illustrates what happens, for example, when the microporous structure collapses in a portion of the sheath of fiber 1a. In fiber 1b, a portion of sheath 4b is an opaque and microporous region 7, but sheath 4b also has a see-through region 9 of lower porosity. In the see-through region 9, the core 6 and its color are visible through the sheath 4b, while the opacity of microporous region 7 continues to hide core 6. Thus, fiber 1b is an embodiment of a multi-component fiber comprising at least first and second components (sheath 4b and core 6, respectively), wherein at least a portion of the second component (core 6) can be seen through at least a portion of the first component (sheath 4b) and an embodiment of a fiber comprising an opaque, microporous region 7 and a see-through region 9 of lower porosity.

Figure 1C:
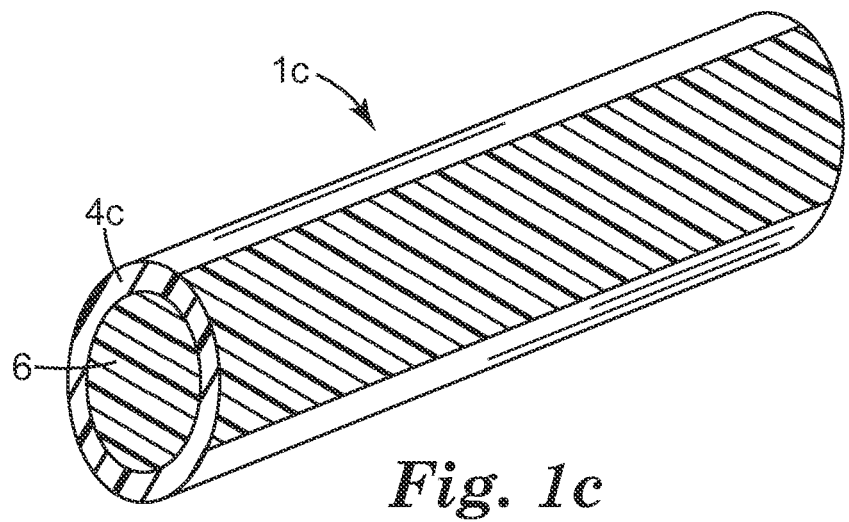
FIG. 1c is a perspective view of another embodiment of a multi-component fiber according to the present disclosure.

Another embodiment of a fiber according to the present disclosure is shown in FIG. 1c. FIG. 1c illustrates what happens, for example, when the microporous structure collapses along the entire portion of the sheath of fiber 1b. In fiber 1c, at least a portion of core 6 (the entire core 6 as illustrated) can be seen through at least a portion of the sheath 4c (the entire sheath 4c as illustrated).

Figure 2A:
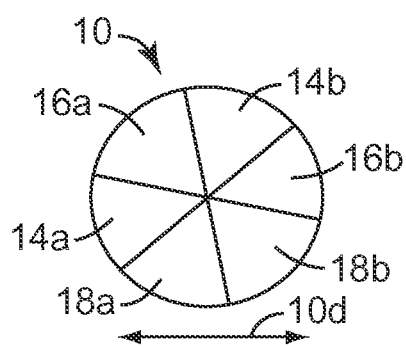
FIGS. 2a to 2d are schematic cross-sections of four embodiments of fibers described herein.
Figure 2B:
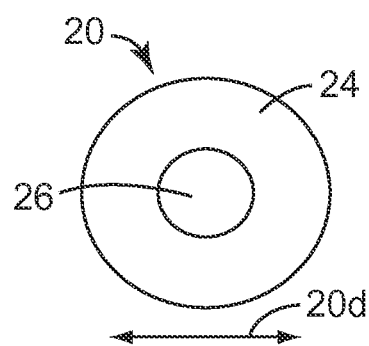
Figure 2C:
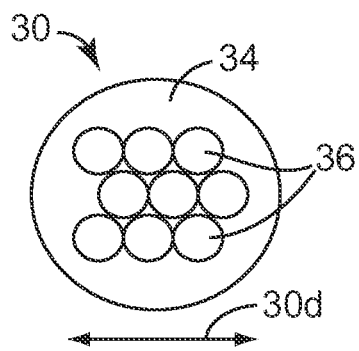
Figure 2D:
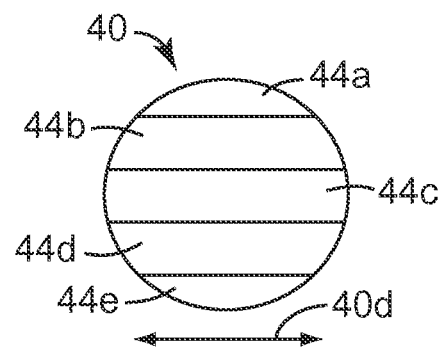

When the fiber according to the present disclosure is a multi-component fiber, the components can be arranged in a variety of configurations. Examples of configurations are shown in FIGS. 2a-2d. A core-sheath configuration, as shown in FIG. 2b or 2c, may be useful, for example, because the external surface of the fiber is typically made from a single composition. It is within the scope of the present disclosure for the core-sheath configurations to have multiple sheaths. Other configurations, for example, as shown in FIGS. 2a and 2d provide options that can be selected depending on the intended application. In the segmented pie wedge (see, e.g., FIG. 2a) and the layered (see, e.g., FIG. 2d) configurations, typically the external surface is made from more than one composition.

Referring to FIG. 2a, a pie-wedge fiber 10 has a circular cross-section "10d". The second component is located in regions 16a and 16b, and the first component is located in regions 14a and 14b. Other regions in the fiber (18a and 18b) may include a third component (e.g., a third, different polymeric composition) or may independently include the same first polymeric composition or second polymeric composition in the first or second components, respectively.

In FIG. 2b, fiber 20 has circular cross-section 20d, sheath 24 providing the first component, and core 26 providing the second component, similar to fibers 1a, 1b, and 1c, described above. FIG. 2c shows fiber 30 having a circular cross-section 30d and a core-sheath structure with sheath 34 providing the first component and plurality of cores 36 providing the second component.

FIG. 2d shows fiber 40 having circular cross-section 40d, with five layered regions 44a, 44b, 44c, 44d, 44e, which provide alternatively at least the first component and the second component. Optionally, a third, different polymeric composition may be included in at least one of the layers.

Figure 3:
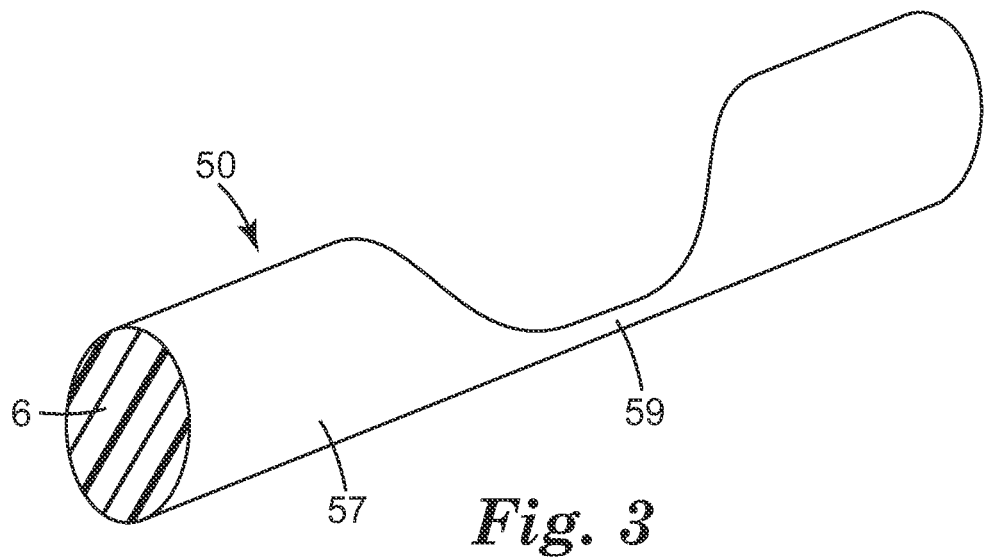
FIG. 3 is a perspective view of another embodiment of a fiber according to the present disclosure, which is not a multi-component fiber.

Another embodiment of a fiber according to the present disclosure is shown in FIG. 3. Fiber 50 includes an opaque, microporous region 57 and a see-through region 59 of lower porosity. When the micropores in region 59 are collapsed according to any of the methods described below, generally the fiber structure is collapsed in that region as shown in fiber 50. The fiber shown in FIG. 3 may be considered a mono-component fiber, formed from a single polymeric material or a single blend of polymers. Mono-component fibers useful in the present disclosure may be solid or hollow. In some embodiments, the fibers according to the present disclosure are solid.

Although only one see-through region of lower porosity 9, 59 is shown in fibers 1b and 50, described above, in other embodiments, there may be a pattern of see-through regions of lower porosity, for example, along the length of the fiber.

There may also be more than one see-through region 9, 59 of lower porosity within the opaque, microporous region 7, 57 that does not necessarily form a repeating pattern. For example, alternating opaque, microporous regions 7, 57 and regions of lower porosity 9, 59 can be made along the length of the fibers. In embodiments of the fibrous webs described below, the portion of any individual fiber that contributes to the see-through region of lower porosity may differ from fiber to fiber (e.g., in size, shape, and pattern). In some embodiments, multiple see-through regions in the form of alphabetical letters can be used together to form a word. The see-through region(s) of lower porosity 9, 59 or, in some embodiments, the pattern of see-through regions of lower porosity can be in the form of a number, picture, symbol, geometric shape, alphabetical letter, bar code, or any combination thereof. Any of these numbers, pictures, symbols, geometric shapes, alphabetical letters, bar codes, or combination thereof may be part of a company name, logo, brand name, or trademark picture if desired.

Referring again to FIG. 3, one looking at see-through region 59 would be able to see what lies beyond it on the other side, while region 57 would still be opaque. See-through region 59 may be useful, for example, when fibers 50 are located in a fibrous web, which will be discussed in further detail, below.

Fibers according to the present disclosure may have a variety of cross-sectional shapes. Useful fibers include those having at least one cross-sectional shape selected from the group consisting of circular, prismatic, cylindrical, lobed, rectangular, polygonal, or dog-boned. The fibers may be hollow or not hollow, and they may be straight or have an undulating shape. Differences in cross-sectional shape allow for control of active surface area, mechanical properties, and interaction with each other or other components. In some embodiments, the fiber according to the present disclosure has a circular cross-section or a rectangular cross-section. Fibers having a generally rectangular cross-sectional shape are also typically known as ribbons. In some embodiments, the fiber according to the present disclosure has a circular cross-section or an elliptical cross-section.

Figure 4:
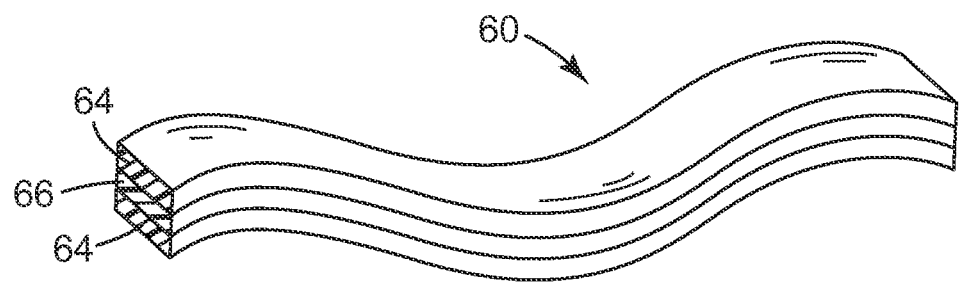
FIG. 4 is a perspective view of another embodiment of a multi-component fiber according to the present disclosure.

Another embodiment of a fiber according to the present disclosure is shown in FIG. 4. FIG. 4 illustrates a ribbon-shaped fiber 60 having a generally rectangular cross-section. In the illustrated embodiment, first and third layers 64 provide the first component on either side of the second layer 66, which provides the second component. In other embodiments, there may be only the first layer 64 and second layer 66. First and third layers 64 may be completely opaque from microvoiding as shown in FIG. 1a or completely see-through as described above in connection with FIG. 1c, or there may be a see-through region in at least one of the first or third layers 64, through which second layer 66 and its color are visible through at least one of first or third layers 64 as described above in connection with FIG. 1b.

In some embodiments, the multi-component fiber of the present disclosure has a core-sheath construction. Such a construction provides the advantage of the microporous sheath substantially surrounding the core. In embodiments in which the sheath and the core are different colors or different shades of the same color, the containment of the core by the sheath in the microporous region allows the color contrast between the microporous region and the at least one see-through region to be more pronounced.

The length-to-width aspect ratio of fibers (in some embodiments, multi-component fibers) according to the present disclosure may be, for example, at least 10:1, 20:1, 25:1, 50:1, 75:1, 100:1, 150:1, 200:1, 250:1, 500:1, 1000:1, or more. When the cross-section of the fiber is rectangular or oblong, the width in the length-to-width aspect ratio may be considered the maximum cross-sectional dimension. The width-to-thickness aspect ratio of fibers (in some embodiments, multi-component fibers) according to the present disclosure may be, for example, up to 10:1, 9:1, 8:1, 7:1, 5:1, 4:1, 3:1, 2:1, 1.5:1, 1.3:1, or 1.1:1. In some embodiments, the width-to-thickness aspect ratio may be in a range from 1.5:1 to 1.1, 1.4:1 to 1:1, 1.3:1 to 1:1, or 1.2:1 to 1:1.

Fibers (in some embodiments, multi-component fibers) according to the present disclosure may have any desired length. For example, the fibers may have a length of at least one mm. In some embodiments, the fibers are considered continuous. In some embodiments, fibers according to the present disclosure may have a length up to 100 mm or 60 mm, in some embodiments, in a range from 2 mm to 60 mm, 3 mm to 40 mm, 2 mm to 30 mm, or 3 mm to 20 mm. Typically, the multi-component fibers disclosed herein have a maximum cross-sectional dimension up to 1000 (in some embodiments, up to 900, 750, 500, 250, 200, 150, 100, 90, 80, 70, 60, 50, 40, or 30) micrometers. For example, the fiber may have a circular cross-section with an average diameter in a range from 1 micrometer to 750 micrometers, 1 micrometer to 500 micrometers, 1 micrometers to 200 micrometers, or 10 micrometers to 100 micrometers. In another example, the fiber may have an elliptical or rectangular cross-section with an average width (i.e., longer cross-sectional dimension) in a range from 1 micrometer to 750 micrometers, 1 micrometer to 500 micrometers, 1 micrometers to 200 micrometers, or 10 micrometers to 100 micrometers.

Fibers described herein can generally be made using techniques known in the art for making fibers. Such techniques include fiber spinning (e.g., melt spinning). In melt spinning, a polymer is heated above its melting point and extruded through the orifices of a spinneret into the air. Below the spinneret, the fibers solidify upon cooling. A modification of the spinneret results in multi-component (e.g., bicomponent) fibers. (See, e.g., U.S. Pat. No. 4,406,850 (Hills), U.S. Pat. No. 5,458,972 (Hagen), U.S. Pat. No. 5,411,693 (Wust), U.S. Pat. No. 5,618,479 (Lijten), and U.S. Pat. No. 5,989,004 (Cook)). Fibers according to the present disclosure can also be made by fibrillation of a film, which may provide fibers having a rectangular cross-section.

Various methods are useful for incorporating porosity into the fibers according to the present disclosure. In some embodiments, the porosity in the fiber, including the fiber in any of the embodiments described above and below and any of the embodiments of a fibrous web or article including the fiber, results from beta-nucleation. Semi-crystalline polyolefins can have more than one kind of crystal structure. For example, isotactic polypropylene is known to crystallize into at least three different forms: alpha (monoclinic), beta (pseudohexangonal), and gamma (triclinic) forms. In melt-crystallized material the predominant form is the alpha or monoclinic form. The beta form generally occurs at levels of only a few percent unless certain heterogeneous nuclei are present or the crystallization has occurred in a temperature gradient or in the presence of shearing forces. The heterogeneous nuclei are typically known as beta-nucleating agents, which act as foreign bodies in a crystallizable polymer melt. When the polymer cools below its crystallization temperature (e.g., a temperature in a range from 60° C. to 120° C. or 90° C. to 120° C.), the loose coiled polymer chains orient themselves around the beta-nucleating agent to form beta-phase regions. The beta form of polypropylene is a meta-stable form, which can be converted to the more stable alpha form by thermal treatment and/or applying stress. Micropores can be formed in various amounts when the beta-form of polypropylene is stretched under certain conditions; see, e.g., Chu et al., "Microvoid formation process during the plastic deformation of β-form polypropylene", *Polymer*, Vol. 35, No. 16, pp. 3442-3448, 1994, and Chu et al., "Crystal transformation and micropore formation during uniaxial drawing of β-form polypropylene film", *Polymer*, Vol. 36, No. 13, pp. 2523-2530, 1995. Pore sizes achieved from this method can range from about 0.05 micrometer to about 1 micrometer, in some embodiments, about 0.1 micrometer to about 0.5 micrometer.

Generally, when the porosity in the fiber is generated from a beta-nucleating agent, the fiber comprises a semi-crystalline polyolefin. Various polyolefins may be useful. Typically the semi-crystalline polyolefin comprises polypropylene. It should be understood that a semi-crystalline polyolefin comprising polypropylene may be a polypropylene homopolymer or a copolymer containing propylene repeating units. The copolymer may be a copolymer of propylene and at least one other olefin (e.g., ethylene or an alpha-olefin having from 4 to 12 or 4 to 8 carbon atoms). Copolymers of ethylene, propylene and/or butylene may be useful. In some embodiments, the copolymer contains up to 90, 80, 70, 60, or 50 percent by weight of polypropylene. In some embodiments, the copolymer contains up to 50, 40, 30, 20, or 10 percent by weight of at least one of polyethylene or an alpha-olefin. The semi-crystalline polyolefin may also be part of a blend of thermoplastic polymers that includes polypropylene. Suitable thermoplastic polymers include crystallizable polymers that are typically melt processable under conventional processing conditions. That is, on heating, they will typically soften and/or melt to permit processing in conventional equipment, such as an extruder, to form a sheet. Crystallizable polymers, upon cooling their melt under controlled conditions, spontaneously form geometrically regular and ordered chemical structures. Examples of suitable crystallizable thermoplastic polymers include addition polymers, such as polyolefins. Useful polyolefins include polymers of ethylene (e.g., high density polyethylene, low density polyethylene, or linear low density polyethylene), an alpha-olefin (e.g, 1-butene, 1-hexene, or 1-octene), styrene, and copolymers of two or more such olefins. The semi-crystalline polyolefin may comprise mixtures of stereo-isomers of such polymers, e.g., mixtures of isotactic polypropylene and atactic polypropylene or of isotactic polystyrene and atactic polystyrene. In some embodiments, the semi-crystalline polyolefin blend contains up to 90, 80, 70, 60, or 50 percent by weight of polypropylene. In some embodiments, the blend contains up to 50, 40, 30, 20, or 10 percent by weight of at least one of polyethylene or an alpha-olefin.

In some embodiments, the fiber according to the present disclosure is made from a polymeric composition comprising a semi-crystalline polyolefin and having a melt flow rate in a range from 0.1 to 10 decigrams per minute, for example, 0.25 to 2.5 decigrams per minute.

When the porosity in the fiber according to the present disclosure is generated from a beta-nucleating agent, the beta-nucleating agent may be any inorganic or organic nucleating agent that can produce beta-spherulites in a melt-formed sheet comprising polyolefin. Useful beta-nucleating agents include gamma quinacridone, an aluminum salt of quinizarin sulphonic acid, dihydroquinoacridindione and quinacridin-tetrone, triphenenol ditriazine, calcium silicate, dicarboxylic acids (e.g., suberic, pimelic, ortho-phthalic, isophthalic, and terephthalic acid), sodium salts of these dicarboxylic acids, salts of these dicarboxylic acids and the metals of Group IIA of the periodic table (e.g., calcium, magnesium, or barium), delta-quinacridone, diamides of adipic or suberic acids, different types of indigosol and cibantine organic pigments, quiancridone quinone, N',N'-dicyclohexil-2,6-naphthalene dicarboxamide (available, for example, under the trade designation "NJ-Star NU-100" from New Japan Chemical Co. Ltd.), anthraquinone red, and bis-azo yellow pigments. The properties of fiber are dependent on the selection of the beta-nucleating agent and the concentration of the beta-nucleating agent. In some embodiments, the beta-nucleating agent is selected from the group consisting of gamma-quinacridone, a calcium salt of suberic acid, a calcium salt of pimelic acid and calcium and barium salts of polycarboxylic acids. In some embodiments, the beta-nucleating agent is quinacridone colorant Permanent Red E3B, which is also referred to as Q-dye. In some embodiments, the beta-nucleating agent is formed by mixing an organic dicarboxylic acid (e.g., pimelic acid, azelaic acid, o-phthalic acid, terephthalic acid, and isophthalic acid) and an oxide, hydroxide, or acid salt of a Group II metal (e.g., magnesium, calcium, strontium, and barium). So-called two component initiators include calcium carbonate combined with any of the organic dicarboxylic acids listed above and calcium stearate combined with pimelic acid. In some embodiments, the beta-nucleating agent is aromatic tri-carboxamide as described in U.S. Pat. No. 7,423,088 (Mäder et al.).

The beta-nucleating agent serves the important functions of inducing crystallization of the polymer from the molten state and enhancing the initiation of polymer crystallization sites so as to speed up the crystallization of the polymer. Thus, the nucleating agent may be a solid at the crystallization temperature of the polymer. Because the nucleating agent increases the rate of crystallization of the polymer, the size of the resultant polymer particles, or spherulites, is reduced.

A convenient way of incorporating beta-nucleating agents into a semi-crystalline polyolefin useful for making a fiber according to the present disclosure is through the use of a concentrate. A concentrate is typically a highly loaded, pelletized polypropylene resin containing a higher concentration of nucleating agent than is desired in the final fiber. The nucleating agent is present in the concentrate in a range of 0.01% to 2.0% by weight (100 to 20,000 ppm), in some embodiments in a range of 0.02% to 1% by weight (200 to 10,000 ppm). Typical concentrates are blended with non-nucleated polyolefin in the range of 0.5% to 50% (in some embodiments, in the range of 1% to 10%) by weight of the total polyolefin content of the microporous fiber or first component of the microporous fiber. The concentration range of the beta-nucleating agent in the final microporous fiber or component may be 0.0001% to 1% by weight (1 ppm to 10,000 ppm), in some embodiments, 0.0002% to 0.1% by weight (2 ppm to 1000 ppm). A concentrate can also contain other additives such as stabilizers, pigments, and processing agents.

The level of beta-spherulites in the semi-crystalline polyolefin can be determined, for example, using X-ray crystallography and Differential Scanning calorimetry (DSC). By DSC, melting points and heats of fusion of both the alpha phase and the beta phase can be determined in a microporous fiber or first component of a fiber disclosed herein. For semi-crystalline polypropylene, the melting point of the beta phase is lower than the melting point of the alpha phase (e.g., by about 10 to 15 degrees Celsius). The ratio of the heat of fusion of the beta phase to the total heat of fusion provides a percentage of the beta-spherulites in a sample. The level of beta-spherulites can be at least 10, 20, 25, 30, 40, or 50 percent, based on the total amount of alpha and beta phase crystals in the fiber or component of the fiber. These levels of beta-spherulites may be found in the fiber or component of the fiber before it is stretched.

In some embodiments, the microporous fiber or microporous first component of the fiber according to the present disclosure, including the fiber in any of the embodiments described above and below and any of the embodiments of a fibrous web or article including the fiber, is formed using a thermally induced phase separation (TIPS) method. This method of making the fiber typically includes melt blending a crystallizable polymer and a diluent to form a melt mixture. The melt mixture is then formed into a fiber and cooled to a temperature at which the polymer crystallizes, and phase separation occurs between the polymer and diluent, forming voids. In this manner a fiber is formed that comprises an aggregate of crystallized polymer and diluent. The voided fiber has some degree of opacity.

In some embodiments, following formation of the crystallized polymer, the porosity of the material is increased by at least one of stretching the fiber in at least one direction or removing at least some of the diluent. This step results in a network of interconnected micropores. This step also permanently attenuates the polymer to form fibrils, imparting strength and porosity to the fiber. The diluent can be removed from the material either before or after stretching. In some embodiments, the diluent is not removed. Pore sizes achieved from this method can range from about 0.2 micrometer to about 5 micrometers.

When the fiber or component of the fiber according to the present disclosure is made microporous using a TIPS process, the fiber or first component of the fiber can comprise any of the semi-crystalline polyolefins described above in connection with fibers and fiber components made by beta-nucleation. In addition, other crystallizable polymers that may be useful alone or in combination include high and low density polyethylene, poly(vinylidine fluoride), poly(methyl pentene) (e.g., poly(4-methylpentene), poly(lactic acid), poly(hydroxybutyrate), poly(ethylene-chlorotrifluoroethylene), poly(vinyl fluoride), polyvinyl chloride, poly(ethylene terephthalate), poly(butylene terephthalate), ethylene-vinyl alcohol copolymers, ethylene-vinyl acetate copolymers, polybuyltene, polyurethanes, and polyamides (e.g., nylon-6 or nylon-66). Useful diluents for providing the fiber or first component of the fiber according to the present disclosure include mineral oil, mineral spirits, dioctylphthalate, liquid paraffins, paraffin wax, glycerin, petroleum jelly, polyethylene oxide, polypropylene oxide, polytetramethylene oxide, soft carbowax, and combinations thereof. The quantity of diluent is typically in a range from about 20 parts to 70 parts, 30 parts to 70 parts, or 50 parts to 65 parts by weight, based upon the total weight of the polymer and diluent.

In some embodiments, the microporous fiber or microporous first component of the fiber according to the present disclosure, including the fiber in any of the embodiments described above and below and any of the embodiments of a fibrous web or article including the fiber, is formed using particulate cavitating agents. Such cavitating agents are incompatible or immiscible with the polymeric matrix material and form a dispersed phase within the polymeric core matrix material before formation and stretching of the fiber. When such a polymer substrate is subjected to stretching, a void or cavity forms around the distributed, dispersed-phase moieties, providing a fiber having a matrix filled with numerous cavities that provide an opaque appearance due to the scattering of light within the matrix and cavities. In these embodiments, the fiber or first component of the fiber according to the present disclosure can comprise any of the polymers described above in connection with TIPS films. The particulate cavitating agents may be inorganic or organic. Organic cavitating agents generally have a melting point that is higher than the melting point of the fiber matrix material. Useful organic cavitating agents include polyesters (e.g., polybutylene teraphthalate or nylon such as nylon-6), polycarbonate, acrylic resins, and ethylene norbornene copolymers. Useful inorganic cavitating agents include talc, calcium carbonate, titanium dioxide, barium sulfate, glass beads, glass bubbles (that is, hollow glass spheres), ceramic beads, ceramic bubbles, and metal particulates. The particle size of cavitating agents is such that at least a majority by weight of the particles comprise an overall mean particle diameter, for example, of from about 0.1 micron to about 5 microns, in some embodiments, from about 0.2 micrometer to about 2 micrometers. (The term "overall" refers to size in three dimensions; the term "mean" is the average.) The cavitating agent may be present in the polymer matrix in an amount of from about 2 weight percent to about 40 weight percent, about 4 weight percent to about 30 weight percent, or about 4 weight percent to about 20 weight percent, based upon the total weight of the polymer and cavitating agent.

Additional ingredients may be included in the fiber or first component of the fiber according to any of the embodiments of the present disclosure, depending on the desired application. For example, surfactants, antistatic agents, ultraviolet radiation absorbers, antioxidants, organic or inorganic colorants, stabilizers, flame retardants, fragrances, nucleating agents other than a beta-nucleating agent, and plasticizers may be included. Many of the beta-nucleating agents described above have a color. Also, colorants may be added, for example, in the form of a color concentrate or a colored master batch.

For the microporous fibers made by any of the methods described above, the fiber is typically stretched to form or enhance the microporous structure. In some embodiments, the stretching increases the fiber's length ("L") at least 1.2 times (in some embodiments, at least 1.5, 2, or 2.5 times). In some embodiments, the stretching increases the fiber's length ("L") up to 5 times (in some embodiments, up to 2.5 times). In some embodiments, the stretching increases the fiber's length ("L") up to 10 times (in some embodiments, up to 20 times or more). Stretching the fiber can be carried out by propelling the fibers over rolls of increasing speed (e.g., on a conveyor belt) or using the method described in the Example, below. Stretching the fiber may be performed at elevated temperatures, for example, up to 150° C. Heating the fiber may allow it to be more flexible for stretching. Heating can be provided, for example, by IR irradiation, hot air treatment, or by performing the stretching in a heat chamber. In some embodiments, stretching the fiber is carried out at a temperature range from 50° C. to 130° C. In some embodiments, stretching the fiber is carried out at room temperature.

As discussed above, in some embodiments, a fiber according to the present disclosure can be made by fibrillating a microporous film. The various additives useful for providing porosity into fibers described above (e.g., beta-nucleating agents, diluents, and fillers) are useful for forming porosity in films. The film is typically stretched to form or enhance the microporous structure. Stretching a film can be carried out on a web biaxially or monoaxially. Biaxial stretching means stretching in two different directions in the plane of the film. Typically, but not always, one direction is the machine direction or longitudinal direction "L", and the other, different direction is the cross direction or width direction "W". Biaxial stretching can be performed sequentially by stretching the film, for example, first in one of the longitudinal or width direction and subsequently in the other of the longitudinal or width direction. Biaxial stretching can also be performed essentially simultaneously in both directions. Monoaxial stretching refers to stretching in only one direction in the plane of the film. Typically, monoaxial stretching is performed in one of the "L" or "W" direction but other stretch directions are also possible.

Stretching a film can be carried out in a variety of ways. When the film is a web of indefinite length, for example, monoaxial stretching in the machine direction can be performed by propelling the film over rolls of increasing speed. The term "machine direction" (MD) as used herein denotes the direction of a running, continuous web of the film. A versatile stretching method that allows for monoaxial, sequential biaxial, and simultaneous biaxial stretching of the film employs a flat film tenter apparatus. Such an apparatus grasps the thermoplastic web using a plurality of clips, grippers, or other film edge-grasping means along opposing edges of the film in such a way that monoaxial, sequential biaxial, or simultaneous biaxial stretching in the desired direction is obtained by propelling the grasping means at varying speeds along divergent rails. Increasing clip speed in the machine direction generally results in machine-direction stretching. Means such as diverging rails generally results in cross-direction stretching. The term "cross-direction" (CD) as used herein denotes the direction which is essentially perpendicular to the machine direction. Monoaxial and biaxial stretching can be accomplished, for example, by the methods and apparatus disclosed in U.S. Pat. No. 7,897,078 (Petersen et al.) and the references cited therein. Flat film tenter stretching apparatuses are commercially available, for example, from Brückner Maschinenbau GmbH, Siegsdorf, Germany. Stretching the film is typically performed at elevated temperatures, for example, up to 150° C. Heating the film may allow it to be more flexible for stretching. Heating can be provided, for example, by IR irradiation, hot air treatment, or by performing the stretching in a heat chamber. In some embodiments, stretching the film is carried out at a temperature range from 50° C. to 130° C.

After stretching, the film may be fibrillated by cutting or using fluid jets, for example.

The present disclosure also provides a fibrous web including multiple fibers as described in any of the above embodiments. The fibrous web may be, for example, a knit, woven, or nonwoven web. In some embodiments, the dimensions of the fibers used together in the fibrous web or article according to the present disclosure, and components making up the fibers are generally about the same, although use of fibers with even significant differences in compositions and/or dimensions may also be useful. In some applications, it may be desirable to use two or more different groups of fibers or multi-component fibers (e.g., at least one different polymer or resin, one or more additional polymers, different average lengths, or otherwise distinguishable constructions), where one group offers a certain advantage(s) in one aspect, and other group a certain advantage(s) in another aspect.

In some embodiments, the fibrous web is a nonwoven web. In some embodiments, the fibrous web is a spunbonded, meltblown, or spunlace nonwoven. The term "spunbonded" refers to small diameter fibers which are formed by extruding molten thermoplastic material as filaments from a plurality of fine, usually circular capillaries of a spinneret with the diameter of the extruded filaments then being rapidly reduced to fibers. The fibers are then directly deposited (e.g., using air streams) onto a collecting belt in a random fashion. Spunbond fibers are generally continuous and have diameters generally greater than about 7 micrometers, more particularly, between about 10 and about 20 micrometers. The term "meltblown" means fibers formed by extruding a molten thermoplastic material through a plurality of fine, usually circular, die capillaries as molten threads or filaments into converging high velocity, usually hot, gas (e.g. air) streams which attenuate the filaments of molten thermoplastic material to reduce their diameter, which may be to microfiber diameter. Thereafter, the meltblown fibers are carried by the high velocity gas stream and are deposited on a collecting surface to form a web of randomly disbursed meltblown fibers. Meltblown fibers are generally microfibers which may be continuous or discontinuous with diameters generally less than 10 micrometers. Spunlacing uses high-speed jets of water to strike a web to intermingle the fibers of the web. Spunlacing is also known as hydroentangling and can be carried out on fibrous webs made, for example, using carded webs and air-laid webs. The term "coform" means a meltblown material to which at least one other material (e.g., pulp or staple fibers) is added during the meltblown web formation.

The nonwoven fibrous web may also be made from bonded carded webs. Carded webs are made from separated staple fibers, which fibers are sent through a combing or carding unit which separates and aligns the staple fibers in the machine direction so as to form a generally machine direction-oriented fibrous nonwoven web. However, randomizers can be used to reduce this machine direction orientation. Once the carded web has been formed, it is then bonded by one or more of several bonding methods to give it suitable tensile properties. One bonding method is powder bonding wherein a powdered adhesive is distributed through the web and then activated, usually by heating the web and adhesive with hot air. Another bonding method is pattern bonding wherein heated calender rolls or ultrasonic bonding equipment are used to bond the fibers together, usually in a localized bond pattern though the web can be bonded across its entire surface if so desired. Generally, the more the fibers of a web are bonded together, the greater the tensile properties of the nonwoven web.

The fibrous web according to the present disclosure may have a variety of basis weights, depending on the desired use of the fibrous web. Suitable basis weights for nonwoven fibrous webs according to the present disclosure may be, for example, 200 grams per square meter (gsm) or less, in a range from 7 gsm to 70 gsm, in a range from 10 gsm to 50 gsm, or in a range from 12 gsm to 30 gsm.

Figure 5:
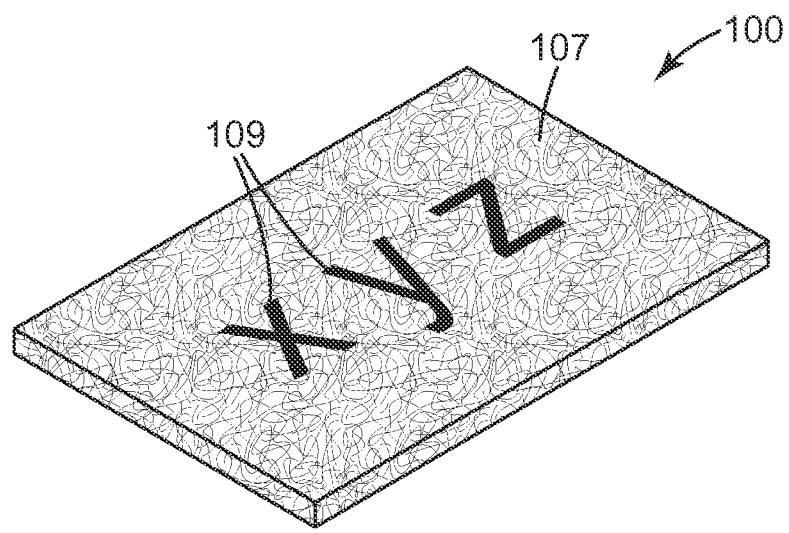
FIG. 5 is a perspective view of an embodiment of a fibrous web according to the present disclosure.

FIG. 5 illustrates an embodiment of a fibrous web according to the present disclosure. Fibrous web 100 may be made, for example, from multiple fibers 1a, described above in connection with FIG. 1a. Fibrous web 100 includes at least one first region 107, in which first portions of the multiple fibers are opaque and microporous, and at least one second region 109, in which second portions of the multiple fibers form a see-through region of lower porosity than the first portions. The second region 109 is in the form of alphabetical letters in the illustrated embodiment. However, as described above, the see-through regions can be in the form of a number, picture, symbol, geometric shape, alphabetical letter, bar code, or any combination thereof. Any of these numbers, pictures, symbols, geometric shapes, alphabetical letters, or combination thereof may be part of a company name, logo, brand name, or trademark picture if desired. In some embodiments of fibrous web 100, the multiple fibers are the same as or similar to fibers 1b shown in FIG. 1b, in which sheath 4b is opaque and microporous in region 7, and core 6 is different from sheath 4a. Core 6 need not be microporous and may have a different color or different shade of the same color as sheath 4a. When the microvoids in the sheath 4b of fibers in the second region 109 are collapsed using the methods described below, the cores 6 of portions of these fibers become visible in the fibrous web. Thus, a different second region 109 may exhibit a different color than the at least one first region 107 because of the exposed portions of the different colored cores. In some embodiments, the first region 107 is white, and cores 6 are colored so that they can be readily seen beneath the second region 109. In these embodiments, since the second portions of the multiple fibers forming the see-through regions of lower porosity are located only in the first component of the multi-component fibers, a large portion of the fiber structure (e.g., thickness) can be retained.

Figure 6:
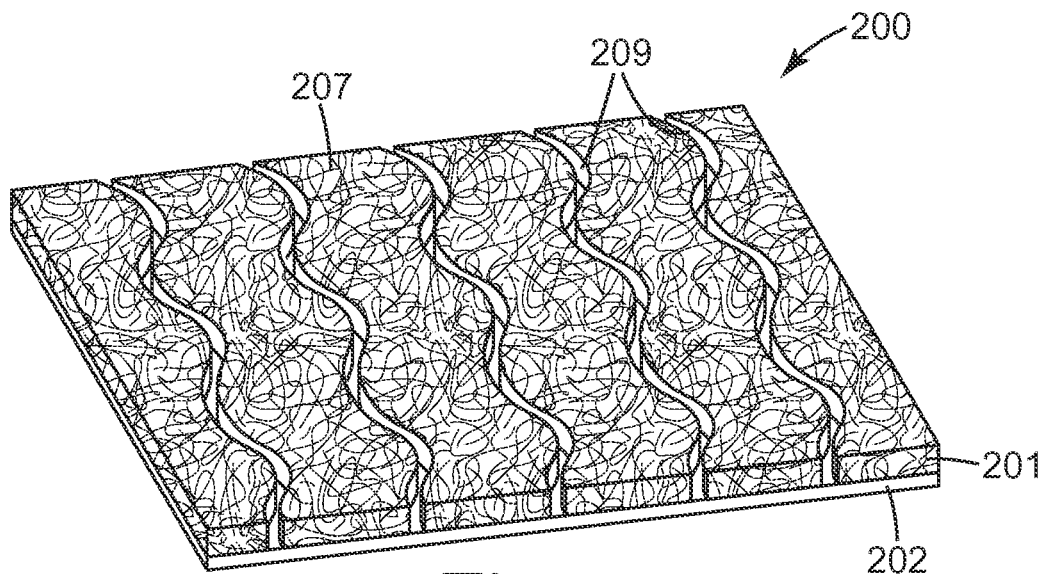
FIG. 6 is a perspective view of an embodiment of a laminate in which a fibrous web according to the present disclosure is a layer.

In some embodiments, the fibrous web according to the present disclosure is a first layer of a laminate comprising the first layer and a second layer, and a portion of the second layer is visible through the second portions of the multiple fibers. FIG. 6 is a perspective view of a laminate 200 in which the fibrous web is a first layer 201. First layer 201 has a first region 207, in which first portions of the multiple fibers are opaque and microporous. First layer 201 also has second region 209, in which second portions of the multiple fibers form a see-through region of lower porosity than the first portions, which in the illustrated embodiment is a pattern of see-through regions of lower porosity. The second layer 202 of the laminate 200 is visible through the second portions of the multiple fibers. The second layer 202 of the laminate 200 may have a contrasting color (e.g., different color or different shade of the same color) that is visible in the second region 209. In some embodiments of laminate 200, the multiple fibers in the first layer 201 are the same as or similar to fibers 50 shown in FIG. 3. When the microvoids in the fibers in the second region 209 are collapsed using the methods described below, the second layer 202 of the laminate can become visible. In some embodiments, the first region 207 is white, and a colored second layer can be readily seen beneath the second region 209.

A multilayer construction such as that shown in FIG. 6 can be made in various ways, and the second layer 202 or other layers can be made from a variety of materials. In some embodiments, the second layer or other layers may comprise woven webs, non-woven webs (e.g., spunbond webs, spunlaced webs, airlaid webs, meltblown web, and bonded carded webs), textiles, plastic films (e.g., single- or multi-layered films, coextruded films, laterally laminated films, or films comprising foam layers), and combinations thereof. The second layer 202 or other layers may be colored with one or more colors (e.g., by printing and/or by inclusion of a pigment or dye). The second layer 202 or other layers may also be metalized. For any of these types of materials, the first and second layer can be joined by extrusion lamination, adhesives (e.g., pressure sensitive adhesives), or other bonding methods (e.g., ultrasonic bonding, thermal bonding, compression bonding, or surface bonding).

When the second layer 202 is a thermoplastic film, it can be made from a variety of suitable thermoplastic materials including polyolefin homopolymers such as polyethylene and polypropylene, copolymers of ethylene, propylene and/or butylene; copolymers containing ethylene such as ethylene vinyl acetate and ethylene acrylic acid; polyesters such as poly(ethylene terephthalate), polyethylene butyrate and polyethylene napthalate; polyamides such as poly(hexamethylene adipamide); polyurethanes; polycarbonates; poly (vinyl alcohol); ketones such as polyetheretherketone; polyphenylene sulfide; and mixtures thereof. In some embodiments, the thermoplastic film includes a colorant such as a pigment or dye.

In some embodiments, the fibrous web according to the present disclosure is joined to a thermoplastic film, and joining the fibrous web and the thermoplastic film comprises impinging heated gaseous fluid (e.g., ambient air, dehumidified air, nitrogen, an inert gas, or other gas mixture) onto a first surface of the fibrous web while it is moving; impinging heated fluid onto a surface of the thermoplastic film while it is moving; and contacting the first surface of the fibrous web with the surface of the thermoplastic film so that the first surface of the fibrous web is melt-bonded (e.g., surface-bonded or bonded with a loft-retaining bond) to the thermoplastic film. Impinging heated gaseous fluid onto the first surface of the fibrous web and impinging heated gaseous fluid on the thermoplastic film may be carried out sequentially or simultaneously. The term "surface-bonded" when referring to the bonding of fibrous materials means that parts of fiber surfaces of at least portions of fibers are melt-bonded to the surface of the thermoplastic film in such a manner as to substantially preserve the original (pre-bonded) shape of the surface of the thermoplastic film, and to substantially preserve at least some portions of the surface of the thermoplastic film in an exposed condition, in the surface-bonded area. Quantitatively, surface-bonded fibers may be distinguished from embedded fibers in that at least about 65% of the surface area of the surface-bonded fiber is visible above the surface of the thermoplastic film in the bonded portion of the fiber. Inspection from more than one angle may be necessary to visualize the entirety of the surface area of the fiber. The term "loft-retaining bond" when referring to the bonding of fibrous materials means a bonded fibrous material comprises a loft that is at least 80% of the loft exhibited by the material before, or in the absence of, the bonding process. The loft of a fibrous material as used herein is the ratio of the total volume occupied by the web (including fibers as well as interstitial spaces of the material that are not occupied by fibers) to the volume occupied by the material of the fibers alone. If only a portion of a fibrous web has the surface of the thermoplastic film bonded thereto, the retained loft can be easily ascertained by comparing the loft of the fibrous web in the bonded area to that of the web in an unbonded area. It may be convenient in some circumstances to compare the loft of the bonded web to that of a sample of the same web before being bonded, for example, if the entirety of fibrous web has the surface of the thermoplastic film bonded thereto. The hot air can be limited so that it does not form a see-through region in the bonding area unless it is desired. Methods and apparatus for joining a continuous web to a fibrous carrier web using heated gaseous fluid may be found in U.S. Pat. Appl. Pub. Nos. 2011-0151171 (Biegler et al.) and 2011-0147475 (Biegler et al.).

Referring again to FIG. 6, in which the fibrous web is a first layer 201 of a laminate 200 comprising the first layer 201 and a second layer 202, and a portion of the second layer 202 is visible through the second region 209, in which second portions of the fibers form at least one see-through region of lower porosity, the second layer 202 may be a side-by-side co-extruded film. Side-by-side co-extruded films can be made by a number of useful methods. For example, U.S. Pat. No. 4,435,141 (Weisner et al.) describes a die with die bars for making a multi-component film having alternating segments in the film cross-direction. A similar process that also includes co-extruding a continuous outer skin layer on one or both outer faces of the side-by-side co-extruded film as described in U.S. Pat. No. 6,669,887 (Hilston et al.) may also be useful. Management of the flow of different polymer compositions into side-by-side lanes can also be carried out using a single manifold die with a distribution plate in contrast to approaches that require multiple dies to achieve side-by-side co-extrusion. Further details about the die and the distribution plate can be found, for example, in U.S. Pat. Appl. Pub. No. 2012/0308755 (Gorman et al.). Side-by-side co-extruded films can also be made by other extrusion dies that comprise a plurality of shims and have two cavities for molten polymer, such as those dies described, for example, in Int. Pat. App. Pub. No. WO 2011/119323 (Ausen et al.) and U.S. Pat. App. Pub. No. 2014/0093716 (Hanschen et al.). Extrusion dies for side-by-side co-extrusion are also available from Nordson Extrusion Dies Industries, Chippewa Falls, Wis. The side-by-side coextruded film may have different colors or different shades of the same color in different lanes so that more than one color can be seen through the second region 209.

For various applications (e.g., in personal hygiene articles as described in further detail below) it may be useful for one or more zones of second layer 202 to comprise one or more elastically extensible materials extending in at least one direction when a force is applied and returning to approximately their original dimension after the force is removed. The term "elastic" refers to any material that exhibits recovery from stretching or deformation. Likewise, "non-elastic" materials, which do not exhibit recovery from stretching or deformation, may be useful for the second layer 202 as well. Examples of elastomeric polymeric compositions which can be useful for making elastic films include thermoplastic elastomers such as ABA block copolymers, polyurethane elastomers, polyolefin elastomers (e.g., metallocene polyolefin elastomers), polyamide elastomers, ethylene vinyl acetate elastomers, and polyester elastomers. An ABA block copolymer elastomer generally is one where the A blocks are polystyrenic, and the B blocks are conjugated dienes (e.g., lower alkylene dienes). The A block is generally formed predominantly of substituted (e.g, alkylated) or unsubstituted styrenic moieties (e.g., polystyrene, poly(alphamethylstyrene), or poly(t-butylstyrene)), having an average molecular weight from about 4,000 to 50,000 grams per mole. The B block(s) is generally formed predominantly of conjugated dienes (e.g., isoprene, 1,3-butadiene, or ethylene-butylene monomers), which may be substituted or unsubstituted, and has an average molecular weight from about 5,000 to 500,000 grams per mole. The A and B blocks may be configured, for example, in linear, radial, or star configurations. An ABA block copolymer may contain multiple A and/or B blocks, which blocks may be made from the same or different monomers. A typical block copolymer is a linear ABA block copolymer, where the A blocks may be the same or different, or a block copolymer having more than three blocks, predominantly terminating with A blocks. Multi-block copolymers may contain, for example, a certain proportion of AB diblock copolymer, which tends to form a more tacky elastomeric film segment. Other elastomers can be blended with block copolymer elastomers provided that the elastomeric properties are not adversely affected. Many types of thermoplastic elastomers are commercially available, including those from BASF under the trade designation "STYROFLEX", from Shell Chemicals under the trade designation "KRATON", from Dow Chemical under the trade designation "PELLETHANE" or "ENGAGE", from DSM under the trade designation "ARNITEL", from DuPont under the trade designation "HYTREL", and more.

The thermoplastic elastomers including tetrablock styrene/ethylene-propylene/styrene/ethylene-propylene described in U.S. Pat. No. 6,669,887 (Hilston et al.) may also be useful.

Referring again to FIG. 6, second layer 202 may be a multilayer thermoplastic film. In some embodiments, the multilayer construction is a multilayer film made, for example, by coextrusion. A multilayer film of at least first and second layers can be coextruded using any suitable type of coextrusion die and any suitable method of film making such as blown film extrusion or cast film extrusion. In some embodiments, a multilayer melt stream can be formed by a multilayer feedblock, such as that shown in U.S. Pat. No. 4,839,131 (Cloeren). For the best performance in coextrusion, the polymeric compositions for each layer can be chosen to have similar properties such as melt viscosity. Techniques of coextrusion are found in many polymer processing references, including Progelhof, R. C., and Throne, J. L., "Polymer Engineering Principles", Hanser/Gardner Publications, Inc., Cincinnati, Ohio, 1993.

In some embodiments, the second layer 202 may be a multilayer construction of an elastic layer of an elastic polymeric composition (described above) between two skin layers that may be less elastic than the elastic polymeric composition. In other embodiments in which the second layer 202 is a multilayer laminate, the film includes one elastic layer and one relatively less elastic skin layer.

In some embodiments in which the second layer 202 is at least partially elastically extensible, laminate 200 is incrementally stretched or otherwise mechanically activated to provide elasticity to the overall laminate. Such a laminate may be useful in a component of a personal hygiene article (described below) that is desirably elastic (e.g., a stretchable ear portion).

A fibrous web such as that shown in FIG. 5 may also be useful in an elastic component of a personal hygiene article when it is used as the nonwoven portion of an elastic nonwoven laminate.

A multilayer laminate according to the present disclosure, such as that shown in FIG. 6, for example, may have more than one fibrous web made by any of the methods described above. For example, a single second layer 202 can have fibrous web layers 201 on both of its surfaces. The single second layer may be colored. In other embodiments, multiple, different-colored layers may be interleaved with multiple fibrous web layers in an alternating fashion. In some embodiments, see-through regions of lower porosity are then made in certain of the fibrous web layers to reveal different colors in one or more see-through regions.

Figure 7:
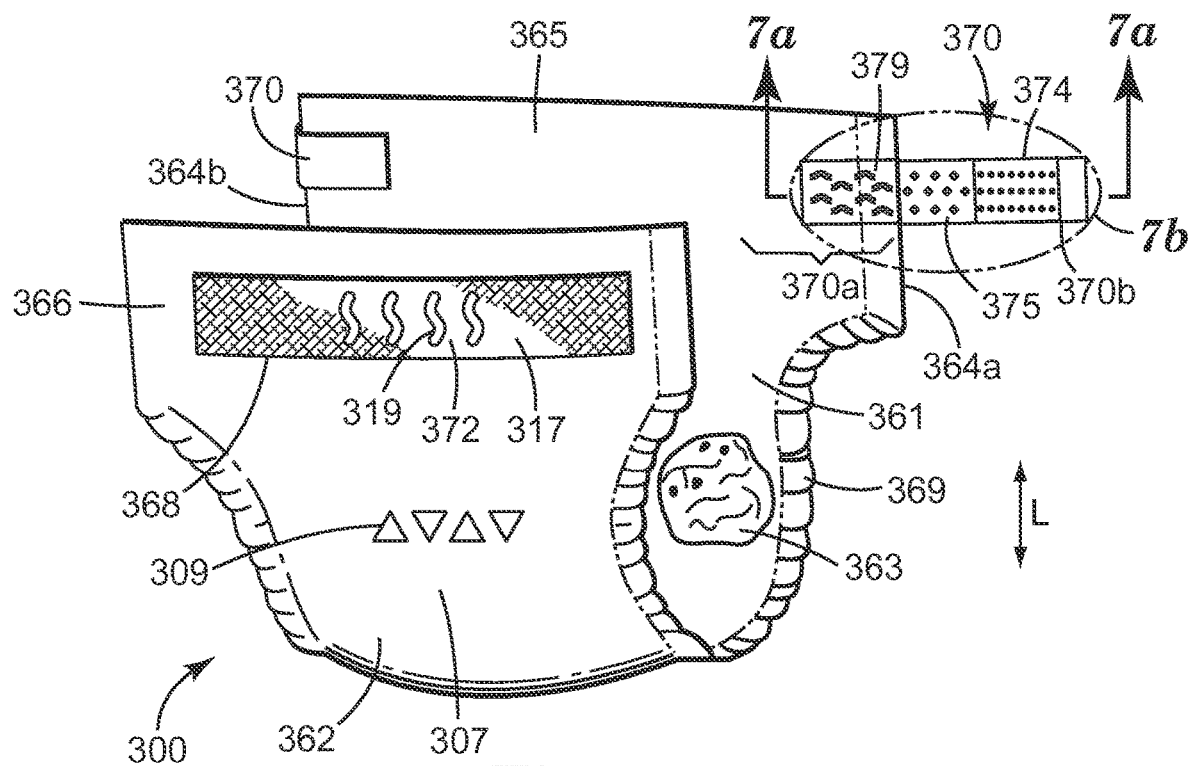
FIG. 7 is a perspective view of an embodiment of a personal hygiene article according to the present disclosure.

The fibrous web according to the present disclosure may be useful, for example, as a component of a personal hygiene article. FIG. 7 is a perspective view of an embodiment of a personal hygiene article according to the present disclosure. The personal hygiene article is a diaper 300 having an essentially hourglass shape. The diaper comprises an absorbent core 363 between a liquid permeable top sheet 361 that contacts the wearer's skin and an outwardly facing liquid impermeable back sheet 362. Diaper 300 has a rear waist region 365 having two fastening tabs 370 arranged at the two longitudinal edges 364a, 364b of diaper 300. Fastening tab 370 has a manufacturer's end 370a secured to the diaper rear waist region 365 and a user's end 370b. The diaper 300 may comprise an elastic material 369 along at least a portion of longitudinal side edges 364a and 364b to provide leg cuffs. When attaching the diaper 300 to a wearer's body, the user's ends 370b of fastening tabs 370 can be attached to a target area 368 comprising fibrous material 372 arranged on the back sheet 362 of the front waist region 366. The longitudinal direction "L" of the personal hygiene article (e.g., diaper 300) refers to the direction that the article extends from the front to rear of the user. Therefore, the longitudinal direction refers to the length of the personal hygiene article between the rear waist region 365 and the front waist region 366. The lateral direction of the personal hygiene article (e.g., diaper 300) refers to the direction that the article extends from the left side to the right side (or vice versa) of the user (i.e., from longitudinal edge 364a to longitudinal edge 364b in the embodiment of FIG. 7).

Figure 7A:
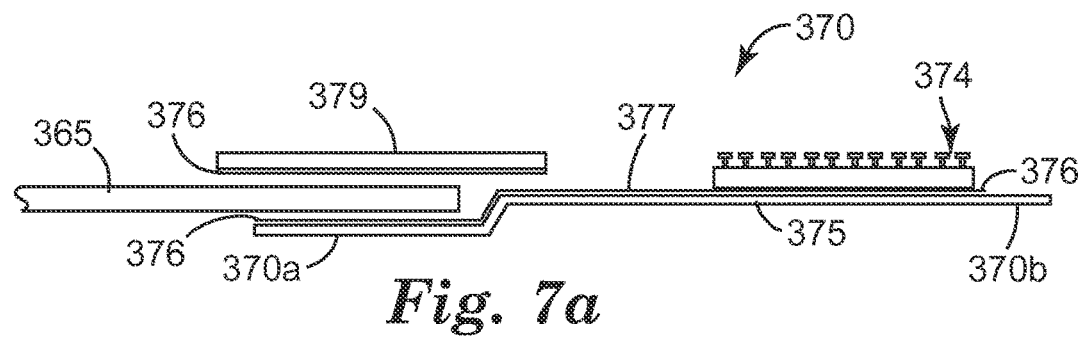
FIG. 7a is an embodiment of an exploded cross-sectional side view taken along line 7a-7a of FIG. 7.

An embodiment of a cross-section of the fastening tab 370 taken through line 7a-7a in FIG. 7 is shown in FIG. 7a. Fastening tab 370 has a manufacturer's end 370a secured to the diaper rear waist region 365 and a user's end 370b that includes the fastening portion. The manufacturer's end 370a corresponds to the part of fastening tab 370 which is fixed or secured to the diaper 300 during the manufacture of the diaper 300. The user's end is typically gripped by the user when attaching the diaper 300 to the wearer and is typically not fixed to the diaper during manufacturing. Fastening tab 370 usually extends beyond longitudinal edges 364a, 364b of the diaper 300.

In the embodiment illustrated in FIG. 7a, fastening tab 370 comprises a tape backing 375 bearing adhesive 376. Adhesive 376 joins optional mechanical fastener 374 to the tape backing 375 and joins the tape backing 375 to the rear waist region 365 of the diaper. In the illustrated embodiment, exposed adhesive 377 may be present between the mechanical fastener 374 and the diaper rear waist region 365. Fastening tab 370 further comprises release tape 379 to contact the exposed part of adhesive 377 when the user's end 370b is folded onto diaper rear waist region 365 (e.g., during packaging and shipping of diaper 300 as shown for the fastening tab 370 at longitudinal edge 364b). As shown in FIG. 7a, the release tape 379 is attached to the tape backing 375 (in some embodiments, directly attached as shown) along only one of its edges, leaving the opposite edge to be joined to the diaper rear waist region 365 during the manufacture of the personal hygiene article. The release tape 379 therefore is generally understood in the art to be permanently attached to the fastening tab 370 and ultimately to the personal hygiene article. In this way, release tape 379 is understood to be different from a release liner that is temporarily placed over exposed adhesive and discarded when the adhesive is in use. The release tape 379 may be joined to the tape backing 375 and diaper rear waist region 365 using adhesive 376 although in some embodiments, thermobonding, ultrasonic bonding, or laser bonding may be useful. Other configurations of release tape 379 are possible depending on the configuration of the attachment of the fastening tab 370 to diaper 300. The tape backing 375 at the user's end 370b of the fastening tab 370 may exceed the extension of the adhesive 376 and optional mechanical fastener 374 thereby providing a fingerlift.

In the open configuration shown in FIG. 7a, the geometry of the tape backing 375 and the release tape 379 results in a Y-shaped bond being formed around the diaper edge 365, which is often referred to in the industry as a Y-bond. However, other configurations of a release surface on a fastening tape are possible, which fastening tapes may or may not include a mechanical fastener. For example, a fastening tape may be partially coated on its second surface with a release coating (e.g., a silicone, fluorochemical, or carbamate coating) and partially coated on its first surface with an adhesive. A fastening tab may be cut from such a tape and attached through its proximal end to the edge of a diaper with its release surface exposed. A distal end of the tab may be folded into a loop so that the adhesive is in contact with the release coating. Such a configuration is described in U.S. Pat. No. 3,930,502 (Tritsch). In another example, the fastening tape may be partially coated with a release coating and partially coated with an adhesive on the same surface. A fastening tab may be cut from the tape and attached through its proximal end to the edge of a diaper with adhesive on its distal end, and the distal end of the tab may be folded back onto itself so that the adhesive is in contact with the release coating. The tape backing may be a continuous piece as shown at 75 in FIG. 7a, or when a stretchable film is desired, for example, there may be two pieces of a backing both attached to an elastic film as described in Int. Pat. Appl. Pub. No. WO 2004/075803 (Loescher et al.). Still other useful configurations of fastening tabs are described in U.S. Pat. Appl. Pub. No. 2007/0286976 (Selen et al.)

FIG. 7 illustrates a variety of embodiments of the fibrous web according to the present disclosure in the same diaper 300. As illustrated in FIG. 7 and the expanded view of the fastening tab 370 shown in FIG. 7b, release tape 379 is a fibrous web having a first region 327 where first portions of multiple fibers in the fibrous web are opaque and microporous and at least one second region 329 where second portions of the multiple fibers form a see-through region. Release tape 379 may be at least partially coated with a release coating (e.g., a silicone, fluorochemical, or carbamate coating). Also, in the illustrated embodiment, tape backing 375 is a fibrous web having a first region 337 where first portions of multiple fibers in the fibrous web are opaque and microporous and at least one second region 339 where second portions of the multiple fibers form a see-through region of lower porosity. Furthermore, target area 368 includes a fibrous web 372 having a first region 317 where first portions of multiple fibers in the fibrous web are opaque and microporous and at least one second region 319 where second portions of the multiple fibers form a see-through region of lower porosity. Finally, backsheet 362 includes a first region 307 where first portions of multiple fibers in the fibrous backsheet are opaque and microporous and at least one second region 309 where second portions of the multiple fibers form a see-through region of lower porosity. Although diaper 300 includes a release tape 379, a tape backing 375, target area 368, and backsheet 362 all including fibrous materials where first regions 307, 317, 327, and 337 comprise first portions of multiple fibers that are opaque and second regions 309, 319, 329, and 339 comprise second portions of the multiple fibers that form a see-through region of lower porosity, any one of these or any combination of two of these may be present in the personal hygiene article according to the present disclosure. Also, other components of the personal hygiene article, alone or in combination with any of the release tape, tape backing, target area, or backsheet in any combination may be formed from a fibrous web according to the present disclosure. Examples of these other components include the topsheet, acquisition/distribution layer, ears, or side panels, which will be described in further detail below.

Figure 7B:
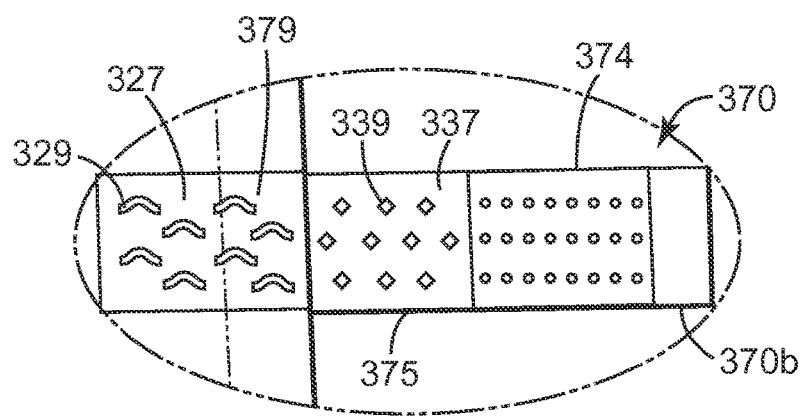
FIG. 7b is an expanded view of the indicated area of FIG. 7.

In some embodiments, including the embodiment shown in FIGS. 7, 7a, and 7b, the fibrous web has an adhesive layer disposed on at least a portion thereof. The adhesive used may be any conventional adhesive, including pressure sensitive adhesives (PSAs) and non-pressure sensitive adhesives. PSAs are well known to those of ordinary skill in the art to possess properties including the following: (1) aggressive and permanent tack, (2) adherence with no more than finger pressure, (3) sufficient ability to hold onto an adherend, and (4) sufficient cohesive strength to be cleanly removable from the adherend. Materials that have been found to function well as PSAs are polymers designed and formulated to exhibit the requisite viscoelastic properties resulting in a desired balance of tack, peel adhesion, and shear holding power. Suitable pressure sensitive adhesives include acrylic resin and natural or synthetic rubber-based adhesives and may be hot melt pressure sensitive adhesives. Illustrative rubber based adhesives include styrene-isoprene-styrene, styrene-butadiene-styrene, styrene-ethylene/butylene-styrene, and styrene-ethylene/propylene-styrene that may optionally contain diblock components such as styrene isoprene and styrene butadiene. The adhesive may be applied using hot-melt, solvent, or emulsion techniques. In FIGS. 7, 7a, and 7b, the adhesive 376 is generally made up of an adhesive having a peel strength that is sufficient to permanently attach the tape backing 375 to the outside surface of a personal hygiene article and, in some embodiments, to permanently attach the mechanical fastener 374 to the tape backing 375. In some embodiments, including the embodiment shown in FIGS. 7, 7a, and 7b, the fibrous web has a mechanical fastener (e.g., a hook strip) joined to at least a portion thereof.

In FIGS. 7 and 7b, each of the release tape 379, tape backing 375, target area 368, and backsheet include a second region 309, 319, 329, and 339 that is included in a pattern of see-through regions of lower porosity although this is not a requirement. There may be more than one see-through region of lower porosity within the first region that does not necessarily form a repeating pattern. For example, multiple see-through regions in the form of alphabetical letters can be used together to form a word. The second region 309, 319, 329, and 339, in some embodiments, can be a plurality of see-through regions of lower porosity in the form of a number, picture, symbol, geometric shape, alphabetical letter, bar code, or any combination thereof. Any of these numbers, pictures, symbols, geometric shapes, alphabetical letters, or combination thereof may be part of a company name, logo, brand name, or trademark picture if desired.

Figure 8:
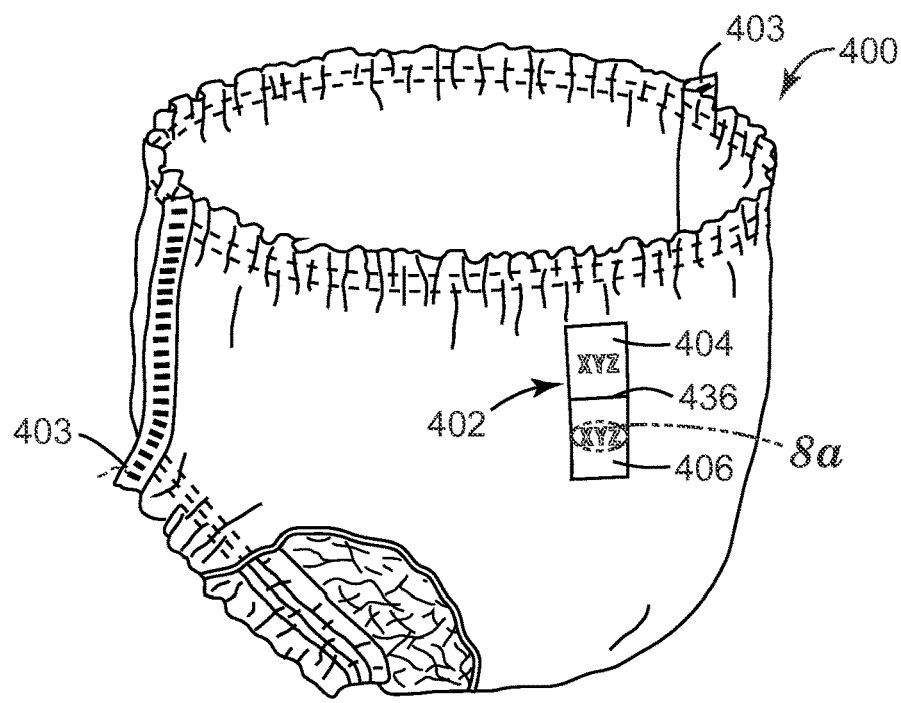
FIG. 8 is a perspective view of another embodiment of personal hygiene article according to the present disclosure.
Figure 8A:
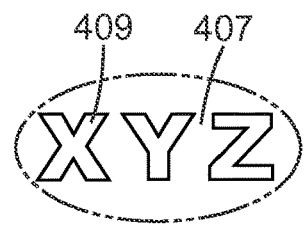
FIG. 8a is an expanded view of the indicated area in FIG. 8.
Figure 8B:
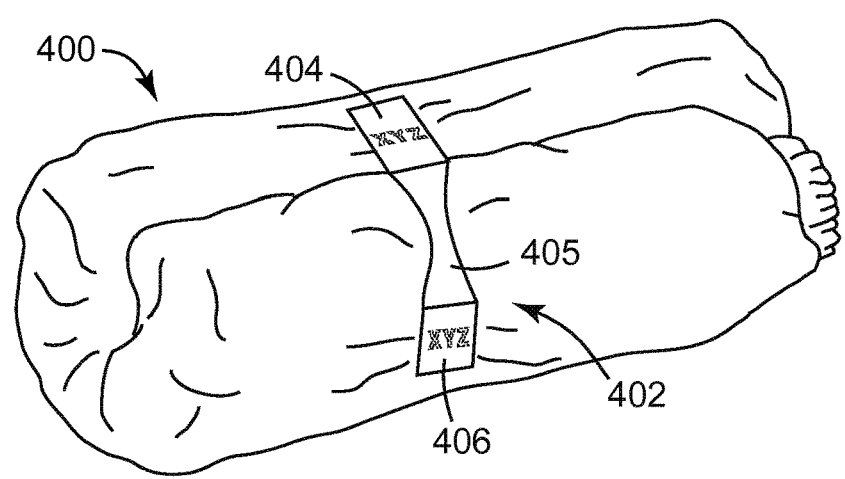
FIG. 8b is a perspective view of the personal hygiene article shown in FIG. 8 rolled up and ready for disposal.

Another embodiment of a personal hygiene article according to the present disclosure is shown in FIG. 8, 8a, or 8b, which illustrates a pants or shorts style incontinence article 400, which may be an infant diaper or adult incontinence article. After use of such a pants style incontinence article, it is typically torn apart along at least one of its seams 403 before rolling it up so that it does not have to be removed over the legs. Article 400 includes a disposal tape 402, which is used to hold a used (soiled) incontinence article in a rolled-up configuration after it has been torn along the seams 403 as shown in FIG. 8b. Although a variety of disposal tape constructions may be useful, in the illustrated embodiment, the disposal tape 402 includes two adjacent first and second tape tab elements 404, 406 separated by slit 436. Each of the first and second tape tab element 404, 406 is adhesively attached to a plastically deformable film 405, which is visible in FIG. 8b. More details about this disposal tape construction can be found in Int. Pat. Appl. Pub. No. WO 2007/032965 (Dahm et al.). In the illustrated embodiment, the tape tab elements 404, 406 each comprise a tab of a fibrous web. Each tab of the fibrous web has a first region 407 where first portions of multiple fibers in the fibrous web are opaque and microporous and at least one second region 409 where second portions of the multiple fibers form a see-through region of lower porosity. The at least one second region 409 is in the form of alphabetical letters in the illustrated embodiment. However, as described above, the see-through regions can be in the form of a number, picture, symbol, geometric shape, alphabetical letter, bar code, or any combination thereof. Any of these numbers, pictures, symbols, geometric shapes, alphabetical letters, or combination thereof may be part of a company name, logo, brand name, or trademark picture if desired.

For any of the embodiments of the portions of personal hygiene articles described above and below, the fibrous web may be a one-layer structure as shown in the embodiment of FIG. 5 or a two-layer laminate as shown in FIG. 6.

In the personal hygiene article according to the present disclosure, the relative areas of the at least one second region in which the second portions of the multiple fibers form a see-through region of lower porosity and the first region in which first portions of the multiple fibers are opaque and microporous may be different in different embodiments. The at least one second region can make up at least 5, 10, 20, 25, 50, 75, or 90 percent a given area of the backsheet, topsheet, release tape, fastening tab backing, loop tape, landing zone area, acquisition layer, disposal tape, side panel or ear. For some patterns (e.g., a pattern of rhombuses or other geometric shapes), the first region may appear as strands separating the second, see-through regions. For other patterns, the second regions may appear more widely separated on a continuous, opaque background.

The various components of a personal hygiene article, such as those described above in connection with FIGS. 7, 7a, 7b, 8, 8a, and 8b, can be made from a variety of suitable materials and assembled together in a variety of ways. In addition to fibrous webs according to the present disclosure, which may be woven webs, knitted webs, and non-woven webs (e.g., spunbond webs, spunlaced webs, airlaid webs, meltblown web, and bonded carded webs), suitable materials for various components of the personal hygiene article may also comprise textiles, plastic films (e.g., single- or multilayered films, coextruded films, laterally laminated films, or films comprising foam layers), and combinations thereof. In some embodiments, fibrous webs according to the present disclosure may be useful as one or more of multiple layers of nonwoven materials including at least one layer of a meltblown nonwoven and at least one layer of a spunbonded nonwoven, or any other suitable combination of nonwoven materials. For example, spunbond-meltbond-spunbond, spunbond-spunbond, or spunbond-spunbond-spunbond multilayer materials may be useful. Composite webs comprising any combination of nonwoven layers and dense film layers may also be useful. As described above, the different layers may have different colors. Fibrous webs according to the present disclosure (e.g., such as that shown in FIG. 5 or 6) may include fibers (e.g., multi-component fibers) according to the present disclosure in combination with other, different fibers, which may be natural fibers (e.g., wood, rayon, or cotton fibers), other synthetic fibers (e.g., thermoplastic fibers made from, e.g., polyethylene, polypropylene, polybutylene, ethylene copolymers, propylene copolymers, butylene copolymers, and copolymers and blends of these polymers), polyesters, and polyamides), or a combination of natural and other synthetic fibers. The components of a personal hygiene article can be assembled by a variety of methods including adhesive bonding, thermobonding, ultrasonic bonding, laser bonding, compression bonding, or surface bonding.

In personal hygiene articles according to the present disclosure, such as that shown in FIG. 7, the topsheet 361 is typically permeable to liquid and designed to contact a wearer's skin, and the outwardly facing backsheet 362 is typically impermeable to liquids. There is typically an absorbent core 363 encased between the topsheet and the backsheet. Various materials can be useful for the topsheet 361, the backsheet 362, and the absorbent core 363 in absorbent articles according to the present disclosure.

Examples of materials useful for topsheets 361 include apertured plastic films, woven fabrics, nonwoven webs, porous foams, and reticulated foams. In some embodiments of the personal hygiene articles according to the present disclosure, at least a portion of the topsheet is made from a fibrous web according to the present disclosure having a first region where first portions of multiple fibers in the fibrous web are opaque and microporous and at least one second region in which second portions of the multiple fibers form a see-through region of lower porosity. In some of these embodiments, the fibrous web is a nonwoven. The fibrous web can be surface treated with a surfactant or otherwise processed to impart the desired level of wettability and hydrophilicity for use as a topsheet.

The backsheet 362 is sometimes referred to as the outer cover and is the farthest layer from the user. The backsheet 362 functions to prevent body exudates contained in absorbent core from wetting or soiling the wearer's clothing, bedding, or other materials contacting the diaper. In some embodiments of the personal hygiene articles according to the present disclosure, at least a portion of the backsheet is made from a microporous film. Such films can provide the advantages of being vapor or gas permeable and substantially impermeable to liquid. In some embodiments, at least portions of the backsheet 362 can include other thermoplastic films (e.g., a poly(ethylene) film). The thermoplastic film may be embossed and/or matte finished to provide a more aesthetically pleasing appearance. In some embodiments of the personal hygiene articles according to the present disclose, at least a portion of the backsheet is made from a fibrous web according to the present disclosure having a first region where first portions of multiple fibers in the fibrous web are opaque and microporous and at least one second region in which second portions of the multiple fibers form a see-through region of lower porosity. The fibrous web may be a woven or nonwoven, for example, laminated to a thermoplastic film or constructed or treated to impart a desired level of liquid impermeability even in the absence of a thermoplastic film. In some embodiments, at least a portion of the backsheet 362 is a nonwoven fibrous web according to the present disclosure that can also be laminated to a colored thermoplastic film or colored nonwoven layer (e.g., a construction that is described above in connection with FIG. 6).

Suitable absorbent cores 363 include natural, synthetic, or modified natural polymers that can absorb and hold liquids (e.g., aqueous liquids). Such polymers can be crosslinked (e.g., by physical entanglement, crystalline domains, covalent bonds, ionic complexes and associations, hydrophilic associations such as hydrogen bonding, and hydrophobic associations or Van der Waals forces) to render them water insoluble but swellable. Such absorbent materials are usually designed to quickly absorb liquids and hold them, usually without release. Examples of suitable absorbent materials useful in absorbent articles disclosed herein include wood pulp or other cellulosic materials and super absorbent polymers (SAP).

Some personal hygiene articles according to the present disclosure include an acquisition layer, which can be useful for quickly accepting an incoming insult and either absorb, hold, channel, or otherwise manage the liquid so that it does not leak outside the article. The acquisition layer may also be referred to, for example, as an acquisition/distribution layer (ADL), a surge layer, intake layer, transfer layer, or transport layer. An acquisition layer is generally capable of handling an incoming insult of between about 60 and 100 milliliters (mL) at an insult volumetric flow rate of from about 5 to 20 mL/second, for infants, for example. An acquisition layer is generally subjacent the topsheet at the surface opposite the user's skin. Various woven and nonwoven webs and foams can be used to construct an acquisition layer. Acquisition layers may be composed of a substantially hydrophobic material, and the hydrophobic material may optionally be treated with a surfactant or otherwise processed to impart a desired level of wettability and hydrophilicity. In some embodiments of the personal hygiene article according to the present disclosure, the acquisition layer is made from a fibrous web according to the present disclosure having a first region where first portions of multiple fibers in the fibrous web are opaque and microporous and at least one second region in which second portions of the multiple fibers form a see-through region of lower porosity. In these embodiments, the fibrous web may be a woven or nonwoven web (in some embodiments, a nonwoven) similar to that shown in FIG. 5.

In some embodiments, the fibrous web according to the present disclosure can be surface treated with a surfactant (e.g., in an amount between about 0.05 and 0.5 weight percent). As described above, a surfactant treatment may be useful if the fibrous web is used as a topsheet or an acquisition/distribution layer. A surfactant can be applied to the fibrous web according to the present disclosure by any conventional means (e.g., spraying, printing, dipping, or brush coating).

In some embodiments, at least a portion of the fibers of the fibrous web according to the present disclosure, which has a first region in which first portions of multiple fibers in the fibrous web are opaque and microporous and at least one second region in which second portions of the multiple fibers form a see-through region of lower porosity, form loops. The fibrous web may therefore be useful as a female mechanical fastening element in a personal hygiene article, for example, and may be a target area or landing zone. The loops may be formed in the fibrous web by any of several methods such as weaving, knitting, warp knitting, weft insertion knitting, circular knitting, or methods for making nonwoven structures. In some embodiments, the loops are included in a nonwoven web or a knitted web. Referring again to FIG. 7, examples of loop tapes that may suitably be applied to the target area 368 to provide a suitable fibrous web 372 for receiving a male mechanical fastener, are disclosed, for example, in U.S. Pat. No. 5,389,416 (Mody et al.) and U.S. Pat. No. 5,256,231 (Gorman et al.) and EP 0,341,993 (Gorman et al.). As described in U.S. Pat. No. 5,256,231 (Gorman et al.), the fibrous layer in a loop material according to some embodiments can comprise arcuate portions projecting in the same direction from spaced anchor portions on a thermoplastic film backing. Any of the fibrous loop materials may be extrusion-bonded, adhesive-bonded, and/or sonically-bonded to a thermoplastic film backing. In other embodiments, the backsheet 362 comprises a woven or nonwoven fibrous layer which is capable of interacting with the user's ends 370b of the tape tabs 370 comprising a strip of male fastening elements. Examples of such backsheets 362 are disclosed, for example, in U.S. Pat. No. 6,190,758 (Stopper) and U.S. Pat. No. 6,075,179 (McCormack et al.).

Personal hygiene articles (e.g., incontinence articles and diapers) according to the present disclosure may have any desired shape such as a rectangular shape, a shape like the letter I, a shape like the letter T, or an hourglass shape. The personal hygiene article may also be a pants-style diaper or refastenable pants-style diaper with fastening tabs 370 along each longitudinal edge. In some embodiments, including the embodiment shown in FIG. 7, the topsheet 361 and backsheet 362 are attached to each other and together form chassis all the way out to the first and second longitudinal opposing edges 364a and 364b. In some embodiments, only one of the topsheet 361 or the backsheet 362 extends to the first and second longitudinal opposing edges 364a and 364b. In other embodiments, the chassis can include separate side panels that are attached to the sandwich of at least topsheet 361, backsheet 362, and absorbent core 363 during manufacturing of the absorbent article, for example, to form ear portions. The side panels can be made of a material that is the same as the topsheet 361 or backsheet 362 or may be made from a different material (e.g., a different nonwoven which may be a fibrous web according to the present disclosure). In these embodiments, the side panels also form part of the chassis. Also, an absorbent article can have two target zones of loop material along the longitudinal edges of the back sheet instead of the large target zone 368 shown in FIG. 7.

The personal hygiene article according to the present disclosure also includes sanitary napkins. A sanitary napkin typically includes a backsheet that is intended to be placed adjacent to the wearer's undergarment. Adhesive or mechanical fasteners are provided on the backsheet to attach the sanitary napkin to the wearer's undergarment. The sanitary napkin typically also includes a topsheet and absorbent core and may include an acquisition layer. The backsheet, topsheet, acquisition layer, and absorbent core can be made from any of the materials described above for these components in diapers or incontinence articles. The sanitary napkin may have any desired shape such as an hourglass, keyhole, or generally rectangular shape. The topsheet and/or backsheet may also include flaps that are intended to wrap around to the opposite side of the wearer's undergarment. At least one of the backsheet, topsheet, acquisition, or other component of the sanitary napkin includes a fibrous web according to the present disclosure which has a first region in which first portions of multiple fibers in the fibrous web are opaque and microporous and at least one second region in which second portions of the multiple fibers form a see-through region of lower porosity. The see-through region of lower porosity or, in some embodiments, the pattern of see-through regions of lower porosity can be in the form of a number, picture, symbol, geometric shape, alphabetical letter, bar code, or any combination thereof. Any of these numbers, pictures, symbols, geometric shapes, alphabetical letters, bar codes, or combination thereof may be part of a company name, logo, brand name, or trademark picture if desired.

The size of any individual see-through area making up the at least one second region in the fibrous web according to the present disclosure may be at least 0.3 mm$^2$, 0.4 mm$^2$, 0.5 mm$^2$, or 0.7 mm$^2$. Generally, if the color contrast between the first region and visible core or layer beneath the any individual see-through area making up the at least one second region is relatively large, smaller individual see-through areas (e.g., 0.3 mm$^2$ to 0.6 mm$^2$) may be easily visible to the naked eye. However, if the color contrast between the first region and visible core or layer beneath the any individual see-through area making up the at least one second region is relatively small, it may be desirable to have larger individual see-through areas (e.g., larger than 0.6 mm$^2$). Also, for fibrous webs having a relatively high basis weight (e.g., greater than 12 gsm or greater than 15 gsm), smaller individual see-through areas (e.g., 0.3 mm² to 0.6 mm²) may be easily visible to the naked eye, while for lower basis weights (e.g., smaller than 15 gsm or smaller than 12 gsm) it may be desirable to have slightly larger individual see-through areas (e.g., larger than 0.6 mm²).

In some embodiments, stretching a fiber according to the present disclosure in order to form or enhance microporosity provides an increase in opacity of the fiber or the first component of the fiber of at least 10, 15, 20, 25, or 30 percent. The increase in opacity may be, for example, up to 100, 90, 85, 80, 75, 70, 65, 60, 55, or 50 percent. The initial opacity is affected, for example, by the thickness of the fiber or first component of the fiber, the composition, and the presence of any fillers or diluents. Stretching typically results in a decrease in thickness, which would typically lead to a decrease in opacity. However, stress whitening and micropore formation leads to an increase in opacity. For the purposes of the present disclosure, opacity can be measured using a spectrophotometer with the "L" value measured separately against a black background and against a white background, respectively. The opacity is calculated as (L measured against the black background/L measured against the white background) times 100. The "L" value is one of three standard parameters in the CIELAB color space scale established by the International Commission on Illumination. "L" is a brightness value, ranging from 0 (black) to 100 (highest intensity). A percentage change in opacity that results from stretching is calculated by [(opacity after stretching−opacity before stretching)/opacity before stretching] times 100.

In some embodiments, stretching a fiber according to the present disclosure in order to form or enhance microporosity provides a decrease in the grayscale value of the fiber or first component of the fiber of at least twenty percent. In some embodiments, stretching provides a decrease in a grayscale value of at least 25, 30, 40, or 50 percent. The decrease in grayscale value may be, for example, up to 90, 85, 80, 75, 70, 65, or 60 percent. For the purposes of this disclosure, the grayscale value is measured in transmission mode using an IMPACT A20 digital camera (PPT Vision, Bloomington, Minn.) equipped with a CMOS (complementary metal oxide semiconductor) image sensor and the IMPACT Software Suite. Stretching a fiber typically results in a decrease in thickness, which would typically lead to an increase in the grayscale value measured in transmission mode. However, stress whitening and micropore formation leads to decrease in transmission mode grayscale values. A percentage change in grayscale value that results from stretching the fiber is calculated by [(grayscale value after stretching−grayscale value before stretching)/grayscale value before stretching] times 100. In some embodiments, the microporous fiber or first component thereof has a grayscale value of up to 40 (in some embodiments, up to 35, 30, 25, 20 or 15). The grayscale values for the microporous fiber disclosed herein may be comparable or better than those achieved for polyolefin films of similar composition but incorporating conventional amounts of IR blocking agents such as titanium dioxide.

The opacity and grayscale measurement of the microporous fiber relate to its ability to transmit light. As used herein, the term "light" refers to electromagnetic radiation, whether visible to the unaided human eye or not. Ultraviolet light is light having a wavelength in a range from about 250 nanometers (nm) to 380 nm. Visible light is light having a wavelength in a range from 380 nanometers (nm) to 700 nm. Infrared light has a wavelength in a range from about 700 nm to 300 micrometers. After the microporous fiber useful for practicing the present disclosure has been stretched, it may have decreased transmission to ultraviolet, visible, and infrared light. The micropores in the stretched fiber tend to scatter light in the ultraviolet, visible, and infrared ranges.

As described above, heat, pressure, or a combination thereof may be useful for providing the see-through regions. In some embodiments, the at least one see-through region of lower porosity had been heated to the melting temperature of the thermoplastic in the microporous fiber. For a semi-crystalline polymer, heating can be carried out at a temperature to melt the crystalline region. Melting the microporous fiber or fibrous web in the at least one see-through region results in a permanent change in the structure of the fiber in the see-through region, which can be accompanied by some shrinkage in that region. In some embodiments, enough heat can be applied to soften the polymer, and pressure can be used to collapse the pores. Heating can be carried out in a press or a heated nip having a raised image of the at least one see-through region so that pressure accompanies the heating to collapse the microporous structure. Pressure alone may provide a temporary change in the microporous structure of the microporous fiber or fibrous web in some instances. When using a static press, it can be useful to use a rubber surface on the film side opposite the side that is exposed to the raised and heated image. The rubber surface can prevent two hard surfaces of the press from forming a hole in the fiber or fibrous web while the see-through region is being made. In a nip, the pressure and gap can be adjusted as well as the line speed to prevent the press from forming holes in the fiber or fibrous web.

Heating may also be carried out with hot air or with a directed radiation source such as a laser. A variety of different types of laser may be useful. For example, a carbon dioxide laser may be useful. An ultraviolet laser and diode laser may also be useful. Suitable wavelengths for the laser can in a range from 200 nm to 11,000 nm. The laser wavelength and absorption properties of the material can be selected to be matched or nearly matched so as to create the heating of material. For a person skilled in the art, the suitable power for the laser, beam size on the material, and speed of the beam movement across the material can be adjusted to achieve the desired heating. This matching of laser and material can be advantageous, for example, when the fibrous web is a layer with a multilayer construction. Heating with the laser can be adjusted to a location of the fibrous web with the multilayer construction (e.g., multilayer film). The heating can be made in a pattern by directing the radiation across the surface to expose an area of material, or the radiation can be directed across the surface of a suitable mask so that a patterned area is exposed to the radiation. The fiber or fibrous web may be positioned outside of the focal plane of the laser to adjust the level of heating.

The microporous regions in the fibrous webs according to the present disclosure may provide advantages other than the contrast between the microporous region and the at least one see-through region that may reveal a different color or different shade of a different color in an underlying component of the fiber or a layer underlying the fibrous web. The ability of the microporous fibers to block the transmission of light (e.g., by scattering) may allow them to be detected in inspection systems that rely upon shining a light onto a substrate and detecting the amount of light received from the area of the irradiated substrate. For example, in the manufacture of a personal hygiene article, the presence or position of a fibrous web disclosed herein or a portion thereof incorporated into the article can be detected because of its ability to block ultraviolet, visible, and/or infrared light. The response of the fibrous web having microporous portions to irradiation by at least one of ultraviolet, visible, or infrared light is evaluated. Subsequently, during manufacturing a personal hygiene article can be irradiated, and at least one of the ultraviolet, visible, or infrared radiation received from the irradiated personal hygiene article can be detected and analyzed for the predefined response of the fibrous web having microporous portions. The position of the fibrous web can be determined using an image analyzer that can detect predefined variations in grayscale values, for example, that correspond to the positions of the fibrous web having microporous portions and other components. The ability of the microporous fiber or fibrous web disclosed herein to scatter infrared light may allow it to be detected even when it is between other layers of materials in the composite article. For more information regarding methods of detecting microporous components in a composite article, see U.S. Pat. App. Pub. No. 2013/0147076 (Chandrasekaran et al.).

Furthermore, microporous fibers tend to have lower densities than their non-microporous counterparts. A low-density nonwoven made from at least partially microporous fibers may feel softer to the touch than a nonwoven having comparable thicknesses but higher densities. The density of the nonwoven can be measured using conventional methods, for example, using helium in a pycnometer. In some embodiments, stretching a fiber containing beta-spherulites provides a decrease in density of at least three percent. In some embodiments, this stretching provides at decrease in density of at least 5 or 7.5 percent. For example, the stretching provides at decrease in density in a range from 3 to 15 percent or 5 to 10 percent. A percentage change in density that results from stretching the fiber is calculated by [(density before stretching−density after stretching)/density before stretching] times 100. The softness of the fibrous web can be measured, for example, using Gurley stiffness.

Fibers and fibrous webs according to the present disclosure may be useful for applications other than the personal hygiene articles described above. In addition to the applications described above, fibrous webs according to the present disclosure may be useful, for example, in medical (e.g., surgical) drapes and gowns, backings for tapes (including for medical applications), geotextile applications (e.g., erosion control textiles), filters, respirators, acoustic insulation, thermal insulation, cleaning wipes, optical diffusers, abrasive articles, medical wraps (e.g., compression wraps), and backings for wound dressings and bandages. The fiber or fibrous web according to the present disclosure may also be useful, for example, as a tamper detector or a heat detector.

In some embodiments, the fibrous web is electrically charged. Electret treatment, for example, can be carried out by a number of different techniques (e.g., those described in U.S. Pat. No. 5,401,446 (Tsai et al.); U.S. Pat. No. 4,215,682 (Kubik et al.); U.S. Pat. No. 4,375,718 (Wadsworth); U.S. Pat. No. 4,592,815 (Nakao); and U.S. Pat. No. 4,874,659 (Ando).

In some embodiments, the fibrous is an insulating material (e.g., acoustically or thermally insulating). For example, the fibrous may comprise a mixture of microfibers and crimped staple fibers as described in U.S. Pat. No. 4,118,531 (Hauser). In some of these embodiments, the fibrous web may include two or more layers of material, for example, in the form of a pad.

For abrasive articles, the fibrous web according to the present disclosure may include abrasive particles dispersed thereon or throughout. Useful abrasives particles may include granules of regular or nonregular shape, of virtually any size, and selected from a broad variety of classes of natural or synthetic, abrasive, mineral particulate, such as silicon carbide, aluminum oxide (e.g., ceramic aluminum oxide, heat-treated aluminum oxide, and white-fused aluminum oxide), cubic boron nitride, ceramic beads or grains such as abrasive materials available from 3M Company, St. Paul, Minn., under the trade designation "CUBITRON", alumina zirconia, diamond, ceria (that is, cerium oxide), garnet, flint, silica, pumice, calcium carbonate, plastic abrasive grains (e.g., made of polyester, polyvinylchloride, methacrylates, polycarbonates, melamine, and polystyrene), crushed plant materials (e.g., shells such as walnut shells and pits such as apricot, peach, and avocado pits), and mixtures of one or more of these materials. The ultimate use of the abrasive article will determine what abrasive particles are most suitable.

For filtration applications, the fibrous web according to the present disclosure may include activated carbon particles dispersed thereon or throughout. Other particles may also be useful in combination the fibrous web for filtration applications. For example, metal ion exchange zeolite sorbents, ion exchange resins, antimicrobial agents, activated alumina, and particulate filter media (e.g., sand) may be useful.

SOME EMBODIMENTS OF THE DISCLOSURE

In a first embodiment, the present disclosure provides a multi-component fiber comprising at least first and second components, wherein at least a portion of the first component is opaque and microporous, and wherein the second component is different from the first component.

In a second embodiment, the present disclosure provides the multi-component fiber of the first embodiment, wherein the first component further comprises a see-through region of lower porosity than the portion that is opaque and microporous.

In a third embodiment, the present disclosure provides the multi-component fiber of the first embodiment, wherein at least a portion of the second component can be seen through the see-through region of lower porosity.

In a fourth embodiment, the present disclosure provides a multi-component fiber comprising at least first and second components, wherein at least a portion of the second component can be seen through at least a portion of the first component.

In a fifth embodiment, the present disclosure provides the multi-component fiber of any one of the first to fourth embodiments, wherein the multi-component fiber is a core-sheath fiber, wherein the sheath comprises the first component, and wherein the core comprises the second component.

In a sixth embodiment, the present disclosure provides the multi-component fiber of any one of the first to fifth embodiments, wherein the first component and second component are different colors or different shades of the same color. For example, the first component can be white and the second component not white.

In a seventh embodiment, the present disclosure provides a fiber comprising an opaque, microporous region and a see-through region of lower porosity.

In an eighth embodiment, the present disclosure provides the fiber of the seventh embodiment, wherein the fiber is solid (in other words, not hollow).

In a ninth embodiment, the present disclosure provides the fiber of the seventh or eighth embodiment, wherein the fiber is a core-sheath fiber, and wherein sheath comprises both the opaque, microporous region and the see-through region of lower porosity.

In a tenth embodiment, the present disclosure provides the multi-component fiber or fiber of any one of the first to ninth embodiments, wherein the first component or the fiber comprises a beta-nucleating agent.

In an eleventh embodiment, the present disclosure provides the multi-component fiber or fiber of any one of the first to tenth embodiments, wherein the first component or the fiber comprises at least one of a filler or a diluent.

In a twelfth embodiment, the present disclosure provides the multi-component fiber or fiber of any one of the first to eleventh embodiments, wherein the first component or the fiber comprises at least one of propylene homopolymer, a copolymer of propylene and other olefins, or a blend of a polypropylene homopolymer and a different polyolefin.

In a thirteenth embodiment, the present disclosure provides the multi-component fiber or fiber of any one of the first to third and fifth to twelfth embodiments, wherein the opaque, microporous regions include closed cell pores.

In a fourteenth embodiment, the present disclosure provides the multi-component fiber or fiber of any one of the first to thirteenth embodiments, wherein the fiber is made by melt spinning.

In a fifteenth embodiment, the present disclosure provides the multi-component fiber or fiber of any one of the first to fourteenth embodiments, wherein the fiber has a width-to-thickness aspect ratio in a range from 1.5:1 to 1:1.

In a sixteenth embodiment, the present disclosure provides a fibrous web comprising multiple fibers of any one of the first to fifteenth embodiments.

In a seventeenth embodiment, the present disclosure provides a fibrous web comprising multiple fibers, the fibrous web comprising at least one first region where first portions of the multiple fibers are opaque and microporous and at least one second region where second portions of the multiple fibers form a see-through region of lower porosity than the first portions.

In an eighteenth embodiment, the present disclosure provides the fibrous web of the seventeenth embodiment, wherein the multiple fibers are multi-component fibers comprising a first component comprising the at least one first region and the at least one second region and a second component, wherein at least a portion of the second component can be seen through the see-through region of lower porosity in the first component.

In a nineteenth embodiment, the present disclosure provides the fibrous web of the eighteenth embodiment, wherein the first component and second component are different colors or different shades of the same color. For example, the first component can be white and the second component not white.

In a twentieth embodiment, the present disclosure provides the fibrous web of the seventeenth or eighteenth embodiment, wherein the fibrous web is a first layer of a laminate comprising the first layer and a second layer, and wherein a portion of the second layer is visible through the second portions of the multiple fibers.

In a twenty-first embodiment, the present disclosure provides the fibrous web of the twentieth embodiment, wherein the first layer and second layer have different colors or different shades of the same color.

In a twenty-second embodiment, the present disclosure provides the fibrous web of the twenty-first embodiment, wherein the first portion of the first layer is white and the second layer is not white.

In a twenty-third embodiment, the present disclosure provides the fibrous web of any one of the sixteenth to twenty-second embodiments, wherein the at least one first region comprises a beta-nucleating agent.

In a twenty-fourth embodiment, the present disclosure provides the fibrous web of any one of the sixteenth to twenty-third embodiments, wherein the at least one first region comprises at least one of a filler or a diluent.

In a twenty-fifth embodiment, the present disclosure provides the fibrous web of any one of the sixteenth to twenty-fourth embodiments, wherein the at least one first region comprises at least one of propylene homopolymer, a copolymer of propylene and other olefins, or a blend of a polypropylene homopolymer and a different polyolefin.

In a twenty-sixth embodiment, the present disclosure provides the fibrous web of any one of the sixteenth to twenty-fifth embodiments, having a release coating disposed on at least a portion thereof.

In a twenty-seventh embodiment, the present disclosure provides the fibrous web of any one of the sixteenth to twenty-sixth embodiments, having an adhesive layer disposed on at least a portion thereof.

In a twenty-eighth embodiment, the present disclosure provides the fibrous web of any one of the sixteenth to twenty-seventh embodiments, having a mechanical fastener joined to at least a portion thereof.

In a twenty-ninth embodiment, the present disclosure provides the fibrous web of any one of the sixteenth to twenty-eighth embodiments, wherein at least a portion of the multiple fibers form loops.

In a thirtieth embodiment, the present disclosure provides the fibrous web of any one of the sixteenth to twenty-ninth embodiments, wherein the fibrous web is a nonwoven web.

In a thirty-first embodiment, the present disclosure provides the fibrous web of the thirtieth embodiment, wherein the nonwoven web comprises a spunbond web.

In a thirty-second embodiment, the present disclosure provides the fibrous web of the thirtieth or thirty-first embodiment, wherein the nonwoven web comprises a meltblown web.

In a thirty-third embodiment, the present disclosure provides the multi-component fiber, fiber, or fibrous web of any one of the first to thirty-second embodiments, wherein the see-through region of lower porosity is included in a pattern of see-through regions of lower porosity within the at least one first region.

In a thirty-fourth embodiment, the present disclosure provides the multi-component fiber, fiber, or fibrous web of any one of the first to thirty-third embodiments, wherein the see-through region of lower porosity is in the form of a number, picture, symbol, geometric shape, alphabetical letter, bar code, or a combination thereof.

In a thirty-fifth embodiment, the present disclosure provides a personal hygiene article comprising a chassis with a topsheet, a backsheet, an absorbent component between the topsheet and the backsheet, wherein the personal hygiene article comprises the fibrous web of any one of the sixteenth to thirty-fourth embodiments.

In an alternative thirty-fifth embodiment, the present disclosure provides a personal hygiene article comprising a chassis with a topsheet, a backsheet, an absorbent component between the topsheet and the backsheet, wherein the personal hygiene article comprises a fiber, and wherein at least a portion of the fiber is opaque and microporous.

In a thirty-sixth embodiment, the present disclosure provides the personal hygiene article of the thirty-fifth embodiment, wherein the personal hygiene article is a diaper or incontinence article.

In a thirty-seventh embodiment, the present disclosure provides the personal hygiene article of the thirty-fifth embodiment, wherein the personal hygiene article is a sanitary napkin.

In a thirty-eighth embodiment, the present disclosure provides the personal hygiene article of any one of the thirty-fifth to thirty-seventh embodiments, wherein the backsheet comprises the fibrous web or the fiber.

In a thirty-ninth embodiment, the present disclosure provides the personal hygiene article of any one of the thirty-fifth to thirty-eighth embodiments, wherein the topsheet comprises the fibrous web or the fiber.

In a fortieth embodiment, the present disclosure provides the personal hygiene article of any one of the thirty-fifth to thirty-eighth embodiments, wherein the personal hygiene article further comprises an acquisition layer between the topsheet and the absorbent core, between the absorbent core and the backsheet, or within the absorbent core, wherein the acquisition layer comprises the fibrous web or the fiber.

In a forty-first embodiment, the present disclosure provides the personal hygiene article of any one of the thirty-fifth to fortieth embodiments, wherein the personal hygiene article further comprises first and second opposing longitudinal edges extending from a rear waist region to an opposing front waist region and a fastening tab attached along the first or second longitudinal edge in the rear waist region or the front waist region, wherein the fastening tab comprises the fibrous web or the fiber.

In a forty-second embodiment, the present disclosure provides the personal hygiene article of any one of the thirty-fifth to forty-first embodiments, wherein the personal hygiene article further comprises first and second opposing longitudinal edges extending from a rear waist region to an opposing front waist region and a side panel attached along the first or second longitudinal edge in the rear waist region or the front waist region, wherein the side panel comprises the fibrous web or the fiber.

In a forty-third embodiment, the present disclosure provides the personal hygiene article of any one of the thirty-fifth to forty-first embodiments, wherein the personal hygiene article further comprises first and second opposing longitudinal edges extending from a rear waist region to an opposing front waist region and an ear attached along the first or second longitudinal edge in the rear waist region or the front waist region, wherein the ear comprises the fibrous web or the fiber.

In a forty-fourth embodiment, the present disclosure provides the personal hygiene article of any one of the thirty-fifth to forty-third embodiments, wherein the personal hygiene article further at least one of a disposal tape or a loop tape, wherein the at least one of the disposal tape or loop tape comprises the fibrous web or the fiber.

In a forty-fifth embodiment, the present disclosure provides a method of making a multi-component fiber according to any one of the first to fifteenth embodiments. The method includes forming a multi-component fiber having a first component and a second component. The first component includes at least one of a beta-nucleating agent, a diluent, or a cavitating agent. The second component is different from the first component. The method further includes stretching the fiber to provide microporosity in at least the first component.

In a forty-sixth embodiment, the present disclosure provides a method of making the fiber of any one of the first to fifteenth embodiments, the method comprising:
providing a fiber, at least a portion of which is microporous; and
collapsing at least some pores in the fiber to form at least one see-through region.

In a forty-seventh embodiment, the present disclosure provides the method of the forty-sixth embodiment, wherein providing the fiber comprises stretching a fiber comprising at least one of a beta-nucleating agent, a filler, or a diluent.

In a forty-eighth embodiment, the present disclosure provides the method of the forty-sixth or forty-seventh embodiment, wherein providing the fiber comprises melt blending a crystallizable polymer and a diluent and cooling to a temperature at which the polymer crystallizes and phase separates from the diluent.

In a forty-ninth embodiment, the present disclosure provides the method of the any one of the forty-sixth to forty-eighth embodiments, wherein collapsing some pores in the fiber comprises heating the fiber to collapse the pores to form the at least one see-through region of lower porosity.

In a fiftieth embodiment, the present disclosure provides the method of the forty-ninth embodiment, wherein heating the fiber is carried out with a heated, patterned roller.

In a fifty-first embodiment, the present disclosure provides the method of the forty-ninth embodiment, wherein heating the fiber is carried out with hot air.

In a fifty-second embodiment, the present disclosure provides the method of the forty-ninth embodiment, wherein heating the fiber is carried out with a laser.

In a fifty-third embodiment, the present disclosure provides a method of making the fibrous web of any one of the sixteenth to thirty-fourth embodiments, the method comprising:
providing the fibrous web, at least a portion of which is microporous; and
collapsing at least some pores in the fibrous web to form at least one see-through region.

In a fifty-fourth embodiment, the present disclosure provides the method of the fifty-third embodiment, wherein collapsing some pores in the fibrous web comprises heating the fibrous web to collapse the pores to form the at least one see-through region of lower porosity.

In a fifty-fifth embodiment, the present disclosure provides the method of the fifty-fourth embodiment, wherein heating the fibrous web is carried out with a heated, patterned roller.

In a fifty-sixth embodiment, the present disclosure provides the method of the fifty-fourth embodiment, wherein heating the fibrous web is carried out with hot air.

In a fifty-seventh embodiment, the present disclosure provides the method of the fifty-fourth embodiment, wherein heating the fibrous web is carried out with a laser.

In a fifty-eighth embodiment, the present disclosure provides the method of the fifty-seventh embodiment, wherein the fibrous web is a layer in a multilayer laminate, and wherein the heating with the laser is adjusted to a location of the fibrous web within the multilayer laminate.

In a fifty-fifth embodiment, the present disclosure provides a method of making a personal hygiene article of any one of the thirty-fifth to forty-fourth embodiments, the method comprising incorporating the fibrous web of any one of the sixteenth to thirty-fourth embodiments into the personal hygiene article.

In order that this disclosure can be more fully understood, the following examples are set forth. It should be understood that these examples are for illustrative purposes only and are not to be construed as limiting this disclosure in any manner.

EXAMPLES

Materials

Film grade polypropylene (PP) copolymer, a polypropylene impact copolymer, was obtained from the Total Petrochemicals, Houston, Tex., under the trade designation "Polypropylene 5571". The polymer density was reported to be 0.905 g/cc as measured according to ASTM D1505 and the melt flow index (MFI) was reported to be 7 (at 230° C. and under the load of 2.16 kg) as measured according to ASTM D1238. The beta nucleating master batch was obtained from the Mayzo Corporation, Alpharetta, Ga., under the trade designation "MPM 1114". The beta nucleating master batch was pelletized and contained a high performance beta nucleant formulation dispersed in a polypropylene homopolymer resin. Blue color masterbatch was obtained from Clariant Corporation Masterbatches Division, Minneapolis, Minn. under the trade designation "PP54643692" described as PP 33:1 PAN 295C dark blue.

Example 1

Multi-component fibers were prepared as generally described in Example 1 of U.S. Pat. No. 4,406,850 (Hills), incorporated herein by reference, except (a) the die was heated to temperature as listed in Table 1; (b) the extrusion die had thirteen orifices per inch laid out on a single row, wherein the die had a transverse length of 330.2 mm (13.0 inches); (c) the hole diameter was 0.794 mm (0.031 in); (d) the relative extrusion rates in grams per hole per minute of the two streams are reported in Table 1; (e) the fibers were conveyed downwards a distance reported in Table 1 and air quenched by compressed air and wound on a core; and (f) the spinning speed was adjusted by a pull roll to rates reported in Table 1.

TABLE 1

| Multi-component Fiber | Core Rate, grams per minute | Sheath Rate, grams per minute | Die Temperature, ° C. | Pull Roll Speed, Meters/minute | Distance to Quench, centimeters |
|---|---|---|---|---|---|
| Fiber 1 | 6.8 | 0.75 | 248 | 1 | 24 |

The core was approximately 500 microns thick and was consisted of 95% polypropylene 5571 with 5% PP54643692. The sheath was approximately 60 microns thick and was made up of 97% of polypropylene 5571 with 3% of MPM 1114. The core material was melted and pumped using a 1" single extruder whereas the sheath material was melted and pumped through a ¾" single screw extruder. Individual strands of fibers were allowed to cool in ambient air and were collected between nylon nonwoven web. The blue color of the core was visible through the sheath of the fiber.

Twenty individual fibers were cut to 4 inches in length. The gauge length between the jaws in the Instron tester (Instron Model 1122 universal testing machine Instron Engineering Corporation, Canton, Mass.) was set to 3 inches. The fibers were stretched to 150% strain. Once 150% strain was reached, the cross head movement was stopped and the load from the fibers was removed by opening one of the jaws so that fibers were loose. After the tension was removed, the fibers were kept taut between the jaws without any load. The stretching was done at room temperature.

As the fibers were stretched, the blue color of the fiber disappeared because of the microporosity formed in the sheath, and eventually the fibers appeared generally white. Once all fibers turned white, hot air was blown using a hair dryer which resulted in the fibers appearing blue again.

Example 2

Fibers were extruded using the equipment and method described in Example 1. Fibers exiting the die were quenched in air and then passed through a hot water bath having a set point of 80° C. The fibers were passed over two rolls operated at different speeds so that the fibers were stretched to four times their original lengths within the free span. This caused the sheaths of the fiber to become microporous and hide the blue color of the cores. The fibers were then rolled up on a common spool.

The fibers were unwound from the common spool and crimped in a stuffing box to give them an undulating shape. The crimper, having model number CL-05, was obtained from DM&E Corporation, Shelby, N.C. Further information about crimping within a stuffing box can be found, for example, in U.S. Pat. No. 5,276,083 (Kawauchi). The crimped fibers were then cut to make staple fiber one inch (2.54 cm) in length. The cutter, having model number 83-351 was obtained from Lummus Industries, Inc., Columbus, Ga. The staple fibers were passed through a combing unit to separate and align the staple fibers which were then air-laid to form a mat. Additional information about air-laying staple fibers can be found in U.S. Pat. No. 5,298,694 (Thompson). The mat was then needle-punched with hot needles to provide entanglements thus forming a fibrous web. Portions of the fibrous web, revealed at the punch-points, exhibited the blue color of the cores.

Example 3

The fibrous web of Example 2 can be passed through a heated embossing roll having indicia thereon. The fibrous web develops indicia where the blue core color is revealed in the places where the embossing roll contacts the fibrous web.

This disclosure may take on various modifications and alterations without departing from its spirit and scope. Accordingly, this disclosure is not limited to the above-described embodiments but is to be controlled by the limitations set forth in the following claims and any equivalents thereof. This disclosure may be suitably practiced in the absence of any element not specifically disclosed herein.

What is claimed is:

1. A multi-component fiber comprising at least first and second components, wherein at least a portion of the first component is opaque and microporous, wherein the second component is different from the first component, wherein the first component further comprises a see-through region of lower porosity than the portion that is opaque and microporous, and wherein at least a portion of the second component can be seen through the see-through region of lower porosity.

2. The multi-component fiber of claim 1, wherein the multi-component fiber is a core-sheath fiber, wherein the sheath comprises the first component, and wherein the core comprises the second component.

3. The multi-component fiber of claim 1, wherein the first component and second component are different colors or different shades of the same color.

4. The multi-component fiber of claim 1, wherein the first component comprises a beta-nucleating agent.

5. The multi-component fiber of claim 1, wherein the first component comprises at least one of propylene homopolymer, a copolymer of propylene and other olefins, or a blend of a polypropylene homopolymer and a different polyolefin.

6. A fibrous web comprising multiple multi-component fibers of claim 1.

7. A personal hygiene article comprising a chassis with a topsheet, a backsheet, an absorbent component between the topsheet and the backsheet, wherein the personal hygiene article comprises the fibrous web of claim 6.

8. A laminate comprising a first layer and a second layer, wherein the first layer is a fibrous web comprising multiple fibers, the fibrous web comprising at least one first region where first portions of the multiple fibers are opaque and microporous and at least one second region where second portions of the multiple fibers form a see-through region of lower porosity than the first portions, and wherein a portion of the second layer is visible through the second portions of the multiple fibers.

9. The laminate of claim 8, wherein the first layer and second layer have different colors or different shades of the same color.

10. The laminate of claim 8, wherein the see-through region of lower porosity is in the form of a number, picture, symbol, geometric shape, alphabetical letter, bar code, or a combination thereof.

11. The laminate of claim 8, wherein the see-through region of lower porosity is included in a pattern of see-through regions of lower porosity within the at least one first region.

12. A personal hygiene article comprising a chassis with a topsheet, a backsheet, an absorbent component between the topsheet and the backsheet, wherein the personal hygiene article comprises the laminate of claim 8.

13. The laminate of claim 8, wherein the fibrous web is a nonwoven web.

14. The laminate of claim 8, wherein the at least one first region comprises at least one of a beta-nucleating agent, a filler, or a diluent.

* * * * *